United States Patent [19]
Fujiyama et al.

[11] Patent Number: 6,117,359
[45] Date of Patent: Sep. 12, 2000

[54] TETRALIN COMPOUND, LIQUID CRYSTAL MATERIAL AND LIQUID CRYSTAL COMPOSITION

[75] Inventors: Takahiro Fujiyama; Toyotaro Maruyama; Yukari Sakai, all of Yokohama, Japan

[73] Assignee: Mitsui Chemicals Inc, Tokyo, Japan

[21] Appl. No.: 09/400,289

[22] Filed: Sep. 21, 1999

[30] Foreign Application Priority Data

Sep. 22, 1998 [JP] Japan .................................. 10-268033

[51] Int. Cl.⁷ .......................... C09K 19/32; C09K 19/12; C07C 69/76
[52] U.S. Cl. ............................... 252/299.62; 252/299.65; 560/102
[58] Field of Search ......................... 252/299.62, 299.65; 560/102

[56] References Cited

U.S. PATENT DOCUMENTS

| | | | |
|---|---|---|---|
| 5,246,222 | 9/1993 | Shimizu et al. | 252/299.62 |
| 5,322,639 | 6/1994 | Kawabata et al. | 252/299.62 |
| 5,356,561 | 10/1994 | Shimizu et al. | 252/299.62 |
| 5,776,365 | 2/2000 | Taatsuki et al. | 252/299.62 |
| 6,019,911 | 2/2000 | Hirano et al. | 252/299.62 |

*Primary Examiner*—C. H. Kelly

[57] ABSTRACT

The invention to provide novel tetralin compounds, liquid crystal materials and liquid crystal compositions, which can constitute a liquid crystal element affording a wide operating temperature range, a high switching speed and a small consumption of electric power as well as a stable contrast.

The tetralin compound of the invention is represented by the following formula [I]

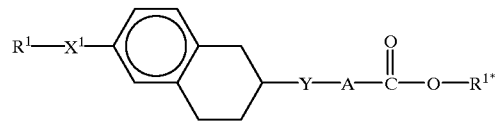

wherein $R^1$ is an alkyl group or a polyfluoroalkyl group of 3–20 carbon atoms (wherein one —$CH_2$— or 2 or more —$CH_2$— or —$CF_2$— not adjacent to each other in these groups may be substituted with —O—), X is —COO—, —O— or a single bond, A is each independently selected from

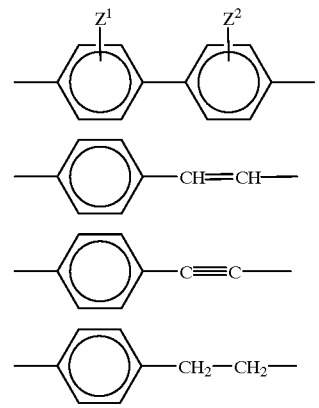

($Z^1$ and $Z^2$ are hydrogen or fluorine), Y is a group selected from —COO—, —$CH_2$O—, —O$CH_2$—, and —$CH_2CH_2$—, $R^{1*}$ is an optically active group represented by the formula —$C^*H$—$(CF_3)$—$(CH_2)_m$—O—$C_nH_{2n+1}$ [II]. (m is an integer of 2–5, and n is an integer of 1–3.).

8 Claims, 5 Drawing Sheets

TETRALIN COMPOUND, LIQUID CRYSTAL MATERIAL AND LIQUID CRYSTAL COMPOSITION

BACKGROUND

Display devices using liquid crystal compounds are used widely at present for not only watches and electronic calculators, but also office automation equipment such as word processors and desktop computers, the automotive navigation system, etc. by dint of their low voltage driveability, very small electric power consumption and compactness as well as thin structure.

Liquid crystal display devices in general use make use of the nematic liquid crystal. The nematic liquid crystal is usually driven in the twisted nematic (TN) mode. It, however, is a drawback of the liquid crystal element driven in the TN mode that the driving margin becomes narrower with an increase in the number of scanning lines, with the result that a sufficient contrast becomes unachievable, and hence, it is difficult to fabricate large-capacity liquid crystal devices. Although the super twisted nematic (STN) mode has been introduced so as to improve such TN mode liquid crystal display device, the STN mode nonetheless poses such problem that both the contrast and response time deteriorate with an increase in the number of scanning lines.

What have attracted a great interest in place of the nematic liquid crystal affording only a slow response time are smectic liquid crystals such as ferroelectric liquid crystals and antiferroelectric liquid crystals. In the display device utilizing these liquid crystals the interaction between the spontaneous polarization inherent to the liquid crystal molecule and the intensity of the applied electric field generates the effective energy to change the direction of molecular orientation of the liquid crystal molecules, and consequentially, the response time is shortened and a high-speed response involving a switching time in the order of microseconds can be attained.

With a liquid crystal element fabricated by sealing the ferroelectric liquid crystal in a cell of a several $\mu$m thickness (surface-stabilized ferroelectric liquid crystal element), two stable states can be secured for an electric field, as described in a technical paper of N.A. Clark et. al. (Appl. Phys. Lett., 36,899 (1980); authors: N. A. Clark and S. T. Lagerwall). The switching time in the electric field between these stable states is very short, namely, in the order of several microseconds. In the case of the antiferroelectric liquid crystal, three stable states prevail, and the tristable switching in this case is also very fast.

With the conventional nematic liquid crystal affording only a slow response speed, there were no other means but the active matrix drive (such as thin-film-transistor (TFT) operation) and the multiline addressing technique (super twisted nematic (STN) operation) to cope with problems associated with the driving. On the other hand, it is an advantage of the ferroelectric liquid crystal and antiferroelectric liquid crystal affording high response speeds that a simple matrix driving technique can be employed.

With regard to the viewing angle of displays, while nematic liquid crystals require an optically compensated film and a special device structure, it is the benefit of smectic liquid crystal that it dispenses with such special provisions.

In order to use such smectic liquid crystals in the display element, there are required such properties as a short response time and a stable contrast in the display device as well as an operating temperature range remaining in the vicinity of room temperature. At present it is difficult to fulmil all of the said properties by a single kind of liquid crystal, and hence a liquid crystal cell is usually prepared by blending several different kinds of liquid crystal. Particularly, as for the response time, a switching speed in the order of 10 some microseconds is requisite.

In order to shorten the response time of the ferroelectric liquid crystal material, it is necessary to increase the spontaneous polarization or to decrease the viscosity.

In antiferroelectric liquid crystal material, it is known that there is a relationship between the threshold voltage and the response time. The lower threshold time is required to shorten the response time.

However, in conventional ferroelectric liquid crystal material, there is a tendency that the static interaction of liquid crystal compounds each other is enlarged according to the increase of spontaneous polarization and consequently the viscosity is increased.

Notwithstanding the aforesaid requirements, the conventional liquid crystal element using antiferroelectric liquid crystal material in most cases has a cell gap of about 2 $\mu$m and cells used for those liquid crystal element were operable with threshold voltage required to electrooptically change such elements in a range of 20–30 V/2 $\mu$m in terms of an absolute value. Considering the fact that the ordinary complementary metal-oxide-semiconductor (CMOS) circuitry is operable at or below 15 V, it is difficult to drive a cell by a CMOS circuitry in a crystal liquid crystal element into which a cell requiring a threshold voltage of such a large absolute value is incorporated.

Additionally, the lower the said threshold voltage is, the larger becomes a deviation from the driving voltage. That is to say, the effective voltage increases with a decline in the threshold voltage. Accordingly, a lower threshold voltage is preferable for the reason that it serves to increase the electrooptical response of a display element. In the light of the aforesaid conditions, there are ardently awaited introduction of such antiferroelectric liquid crystal elements that have a practicably lowest absolute value of threshold voltage, for example, at or below 15 V/2 $\mu$m and are capable of driving the cell at a large effective voltage.

SUMMARY

The present invention has been made for the purpose of resolving such problems associated with the conventional techniques as described above, and it is the object of the invention to provide novel liquid crystal compounds which can be utilized as excellent liquid crystal materials, liquid crystal compositions composed of such compounds. More particularly, it is the object of the invention to provide novel tetralin compounds, liquid crystal materials and liquid crystal compositions, which can constitute a liquid crystal element affording a wide operating temperature range, a high switching speed and a small consumption of electric power as well as a stable contrast.

Specifically, when the novel tetralin compounds of the invention are used, the response time of smectic liquid crystal compositions such as ferroelectric/antiferroelectric liquid crystals become controllable.

The present invention provides novel tetralin compounds, namely, carboxylic acid ester having the tetralin structure.

When the novel tetralin compound of the invention is added to antiferroelectric liquid crystal, there can be provided a liquid crystal composition which can constitute a liquid crystal element equipped with such a cell that imparts a practicably lowest absolute value of a threshold voltage required to electrooptically change the liquid crystal element, for example, at or below 15 V/2 μm, and can drive the element by a large effective voltage.

In cases where the novel tetralin compound of the invention is added to a ferroelectric liquid crystal, there can be provided a liquid crystal composition capable of constituting a liquid crystal element having a short response time with a large degree of spontaneous polarization without increase of the viscosity.

The tetralin compound of the invention is represented by the following formula [I]

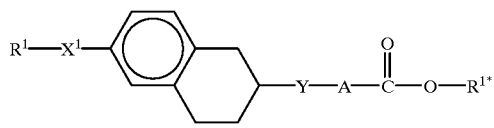

wherein
  $R^1$ is an alkyl group or a polyfluoroalkyl group of 3–20 carbon atoms (wherein one —$CH_2$— or 2 or more —$CH_2$— or —$CF_2$— not adjacent to each other in these groups (hereinafter referred to simply as "2 or more mutually nonadjacent such-and-such groups") may be substituted with —O—),
  $X^1$ is —COO—, —O— or a single bond,
  A is each independently selected from a group consisting of

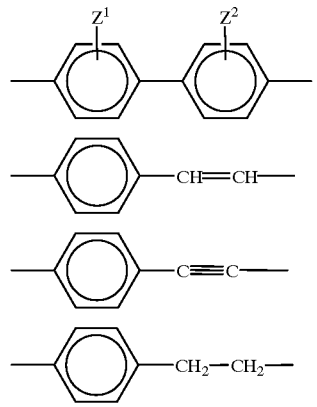

(wherein $Z^1$ and $Z^2$ are each independently a hydrogen atom or a fluorine atom),
  Y is a group selected from the group consisting of —COO—, —$CH_2$O—, —O$CH_2$—, and —$CH_2CH_2$—,
  $R^{1*}$ is an optically active group represented by the following formula [II]

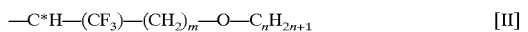
$$—C^*H—(CF_3)—(CH_2)_m—O—C_nH_{2n+1} \quad [II]$$

(wherein m is an integer of 2–5, and n is an integer of 1–3.).

And, there is provided by the invention a liquid crystal material comprising a tetralin compound represented by the formula [I] above.

There is also provided by the invention a liquid crystal composition comprising the tetralin compound represented by the formula [I] above and other liquid crystal compounds and/or additives.

There is further provided by the invention a ferroelectric liquid crystal composition comprising the tetralin compound represented by the formula [I] above and other liquid crystal compounds and/or additives.

There is also provided by the invention an antiferroelectric liquid crystal composition comprising the tetralin compound represented by the formula [I] above and a compound represented by the following formula [III].

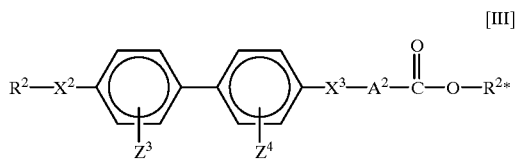

wherein
  $R^2$ is an alkyl group or a polyfluoroalkyl group of 3–20 carbon atoms (wherein one —$CH_2$— or 2 or more mutually nonadjacent —$CH_2$— or —$CF_2$— may be substituted with —O—),
  $A^2$ is a group selected from the group consisting of

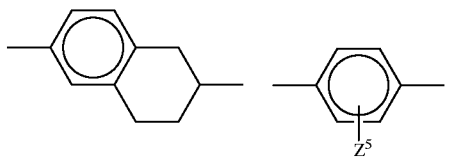

$Z^3$, $Z^4$ and $Z^5$ are each independently a hydrogen atom and a fluorine atom,
  $X^2$ is —COO—, —O—, or a single bond, $X^3$ is —COO—, or —$CH_2$O—, and $R^{2*}$ is an optically active group represented by the following formula [IV] (wherein when V is $CF_3$, p=1 and r≠0, or p=0 and r=0; and when V is $CH_3$, p=0 and r=0).

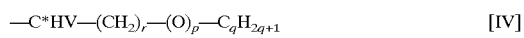
$$—C^*HV—(CH_2)_r—(O)_p—C_qH_{2q+1} \quad [IV]$$

DESCRIPTION OF THE INVENTION

Figure 1:
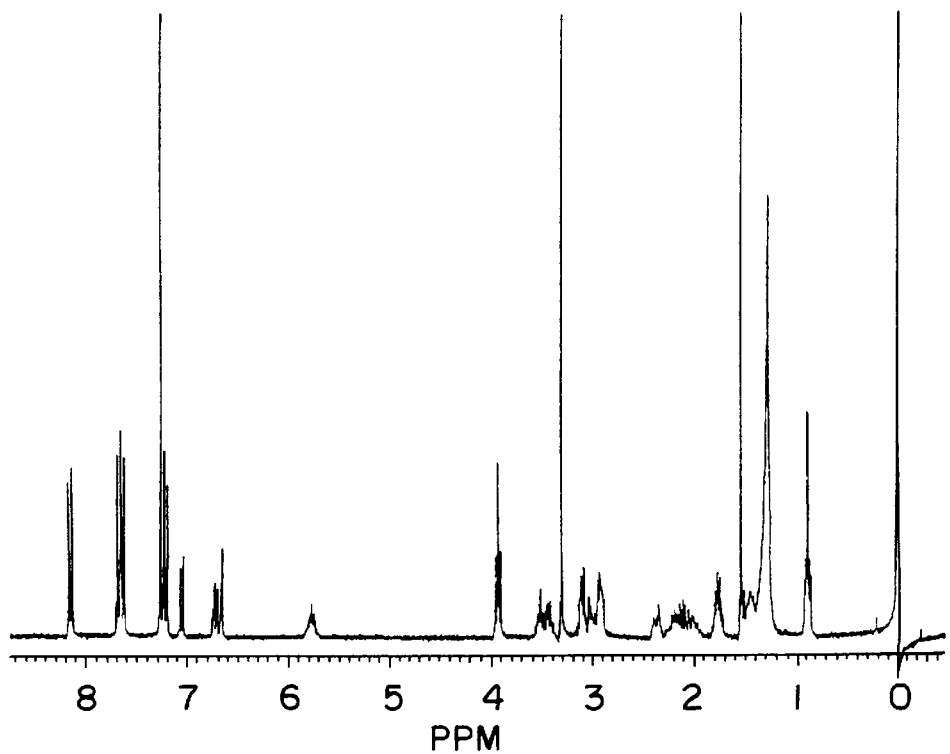
FIG. 1 shows a $^1$H-NMR spectrum of 4'-(6-decyloxy-1,2,3,4-tetrahydro-2-naphthalenecarbonyloxy)-4-biphenylcarboxylic acid (R)-1-trifluoromethyl-3-methoxypropyl ester.

Described in detail below are the tetralin compound, and the liquid crystal material and the liquid crystal composition comprising the tetralin compound of the invention.

Tetralin Compound and Liquid Crystal Material

The tetralin compound of the invention is carboxylic acid ester represented by the following formula [I].

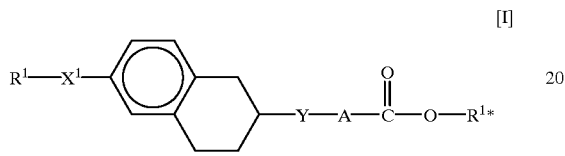

[I]

wherein $R^1$ is an alkyl group or a polyfluoroalkyl group of 3–20 carbon atoms. (wherein one —$CH_2$— or 2 or more mutually nonadjacent —$CH_2$— or —$CF_2$— may be substituted with —O—);

In case that $R^1$ is an alkyl group of 3–20 carbon atoms, this allyl group may take any of a straight-chain form, a branched form and an alicyclic form. However, the molecule of the tetralin compound wherein $R^1$ is a straight-chain alkyl group exhibits excellent liquid crystal characteristics by virtue of its linearly extended rigid straight structure. Concrete examples of such straight-chain alkyl group include hexyl, heptyl, octyl, nonyl, decyl, undecyl, dodecyl, tetradecyl, hexadecyl and octadecyl groups.

Examples of $R^1$ being a polyfluoroalkyl group of 3–20 carbon atoms include groups obtained by substituting part or all of the hydrogen atoms in the above-mentioned alkyl group with fluorine atoms.

There can be cited as examples of such alkyl group that has its one or 2 or more mutually nonadjacent —$CH_2$— or —$CF_2$— substituted with —O—, 10-methoxydecyloxy group, 10-ethoxydecyloxy group and 11-methoxyundecyloxy group.

In the formula [I], $X^1$ is a group selected from the group consisting of —COO— and —O—, or a single bond. Among the above examples, $X^1$ is preferably —O— or a single bond in view of the intended crystallinity and physical characteristics in case the tetralin compound of the invention is used as a liquid crystal material.

In the formula [I], Y is a group selected from the group consisting of —COO—, —$CH_2$O—, —O$CH_2$— and —$CH_2CH_2$—. Among those groups Y is preferably —COO— or —$CH_2$O— in case the ester of the invention is used as a liquid crystal compound.

In the formula [I], $R^{1*}$ is an optically active group represented by the following formula [II].

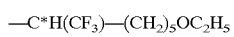

[II]

wherein m is an integer of 2–5 and n is an integer of 1–3;

Among them $R^{1*}$ is preferably a group selected from the group consisting of

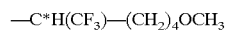

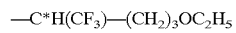

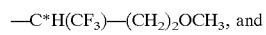

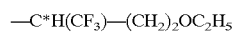

Among these group, preferred are the following groups in view of their properties in case the tetralin compound of the invention is used as a liquid crystal material.

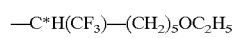

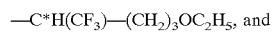

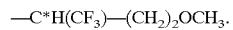

In the formula [I], A is a group selected from the group consisting of

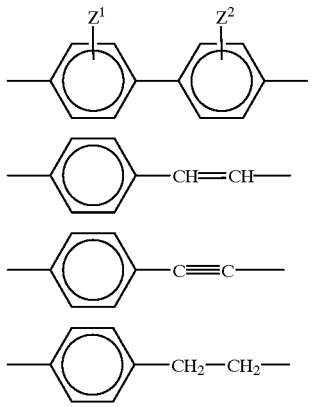

In the group of

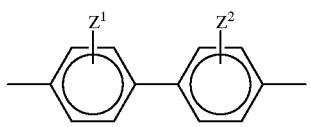

$Z^1$ and $Z^2$ are each independently a hydrogen atom or a fluorine atom. There can be cited as examples thereof,

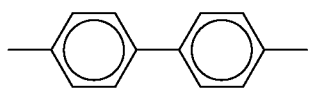

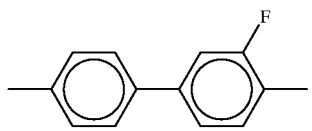

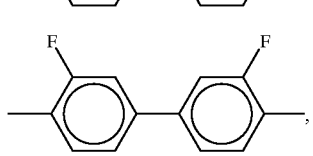

and among which preferred one are

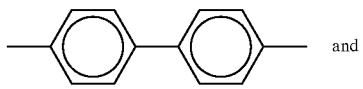

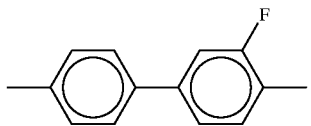

There can be cited as specific examples of ester having the tetralin structure represented by the above formula [I] derived from crboxylic acid those compounds set forth in Table 1 below.

In the below-cited Tables, $R^1$, $R^{1*}$, $X^1$, Y, and A are the groups appealing in the formula [I], and there is no limitation as to the mode of linkage with the tetralin structure.

TABLE 1

| Cpd No. | $R^1$ | $X^1$ | Y | A | $R^{1*}$ |
|---|---|---|---|---|---|
| 1 | $C_{10}H_{21}$ | O | COO | biphenyl | $-C^*H(CF_3)(CH_2)_5OC_2H_5$ |
| 2 | " | " | " | " | $-C^*H(CF_3)(CH_2)_4OCH_3$ |
| 3 | " | " | " | " | $-C^*H(CF_3)(CH_2)_3OC_2H_5$ |
| 4 | " | " | " | " | $-C^*H(CF_3)(CH_2)_2OCH_3$ |
| 5 | " | " | " | " | $-C^*H(CF_3)(CH_2)_2OC_2H_5$ |
| 6 | $C_{10}H_{21}$ | Single bond | COO | biphenyl | $-C^*H(CF_3)(CH_2)_5OC_2H_5$ |
| 7 | " | " | " | " | $-C^*H(CF_3)(CH_2)_4OCH_3$ |
| 8 | " | " | " | " | $-C^*H(CF_3)(CH_2)_3OC_2H_5$ |
| 9 | " | " | " | " | $-C^*H(CF_3)(CH_2)_2OCH_3$ |
| 10 | " | " | " | " | $-C^*H(CF_3)(CH_2)_2OC_2H_5$ |
| 11 | $C_{10}H_{21}$ | COO | COO | biphenyl | $-C^*H(CF_3)(CH_2)_5OC_2H_5$ |
| 12 | " | " | " | " | $-C^*H(CF_3)(CH_2)_4OCH_3$ |
| 13 | " | " | " | " | $-C^*H(CF_3)(CH_2)_3OC_2H_5$ |
| 14 | " | " | " | " | $-C^*H(CF_3)(CH_2)_2OCH_3$ |
| 15 | " | " | " | " | $-C^*H(CF_3)(CH_2)_2OC_2H_5$ |

TABLE 2

| Cpd No. | $R^1$ | $X^1$ | Y | A | $R^{1*}$ |
|---|---|---|---|---|---|
| 16 | $C_{10}H_{21}$ | O | $CH_2O$ | 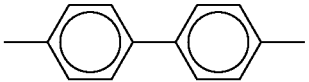 | —$C^*H(CF_3)(CH_2)_5OC_2H_5$ |
| 17 | " | " | " | " | —$C^*H(CF_3)(CH_2)_4OCH_3$ |
| 18 | " | " | " | " | —$C^*H(CF_3)(CH_2)_3OC_2H_5$ |
| 19 | " | " | " | " | —$C^*H(CF_3)(CH_2)_2OCH_3$ |
| 20 | " | " | " | " | —$C^*H(CF_3)(CH_2)_2OC_2H_5$ |
| 21 | $C_{10}H_{21}$ | Single bond | $CH_2O$ | 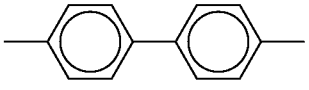 | —$C^*H(CF_3)(CH_2)_5OC_2H_5$ |
| 22 | " | " | " | " | —$C^*H(CF_3)(CH_2)_4OCH_3$ |
| 23 | " | " | " | " | —$C^*H(CF_3)(CH_2)_3OC_2H_5$ |
| 24 | " | " | " | " | —$C^*H(CF_3)(CH_2)_2OCH_3$ |
| 25 | " | " | " | " | —$C^*H(CF_3)(CH_2)_2OC_2H_5$ |
| 26 | $C_{10}H_{21}$ | COO | $CH_2O$ | 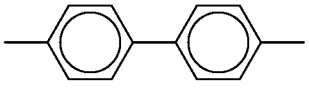 | —$C^*H(CF_3)(CH_2)_5OC_2H_5$ |
| 27 | " | " | " | " | —$C^*H(CF_3)(CH_2)_4OCH_3$ |
| 28 | " | " | " | " | —$C^*H(CF_3)(CH_2)_3OC_2H_5$ |
| 29 | " | " | " | " | —$C^*H(CF_3)(CH_2)_2OCH_3$ |
| 30 | " | " | " | " | —$C^*H(CF_3)(CH_2)_2OC_2H_5$ |

TABLE 3

| Cpd No. | $R^1$ | $X^1$ | Y | A | $R^{1*}$ |
|---|---|---|---|---|---|
| 31 | $C_{10}H_{21}$ | O | COO | 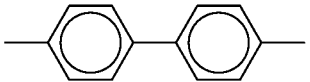 | —$C^*H(CF_3)(CH_2)_5OC_2H_5$ |
| 32 | " | " | " | " | —$C^*H(CF_3)(CH_2)_4OCH_3$ |
| 33 | " | " | " | " | —$C^*H(CF_3)(CH_2)_3OC_2H_5$ |
| 34 | " | " | " | " | —$C^*H(CF_3)(CH_2)_2OCH_3$ |
| 35 | " | " | " | " | —$C^*H(CF_3)(CH_2)_2OC_2H_5$ |
| 36 | $C_{10}H_{21}$ | Single bond | COO | 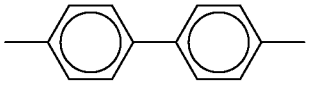 | —$C^*H(CF_3)(CH_2)_5OC_2H_5$ |
| 37 | " | " | " | " | —$C^*H(CF_3)(CH_2)_4OCH_3$ |
| 38 | " | " | " | " | —$C^*H(CF_3)(CH_2)_3OC_2H_5$ |
| 39 | " | " | " | " | —$C^*H(CF_3)(CH_2)_2OCH_3$ |
| 40 | " | " | " | " | —$C^*H(CF_3)(CH_2)_2OC_2H_5$ |

TABLE 3-continued

| Cpd No. | R¹ | X¹ | Y | A | R¹* |
|---|---|---|---|---|---|
| 41 | $C_{10}H_{21}$ | COO | COO | 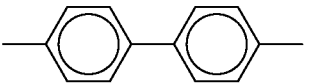 | —C*H(CF$_3$)(CH$_2$)$_5$OC$_2$H$_5$ |
| 42 | " | " | " | " | —C*H(CF$_3$)(CH$_2$)$_4$OCH$_3$ |
| 43 | " | " | " | " | —C*H(CF$_3$)(CH$_2$)$_3$OC$_2$H$_5$ |
| 44 | " | " | " | " | —C*H(CF$_3$)(CH$_2$)$_2$OCH$_3$ |
| 45 | " | " | " | " | —C*H(CF$_3$)(CH$_2$)$_2$OC$_2$H$_5$ |

TABLE 4

| Cpd No. | R¹ | X¹ | Y | A | R¹* |
|---|---|---|---|---|---|
| 46 | $C_{10}H_{21}$ | O | CH$_2$O | 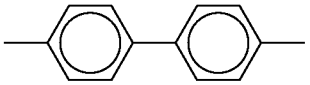 | —C*H(CF$_3$)(CH$_2$)$_5$OC$_2$H$_5$ |
| 47 | " | " | " | " | —C*H(CF$_3$)(CH$_2$)$_4$OCH$_3$ |
| 48 | " | " | " | " | —C*H(CF$_3$)(CH$_2$)$_3$OC$_2$H$_5$ |
| 49 | " | " | " | " | —C*H(CF$_3$)(CH$_2$)$_2$OCH$_3$ |
| 50 | " | " | " | " | —C*H(CF$_3$)(CH$_2$)$_2$OC$_2$H$_5$ |
| 51 | $C_{10}H_{21}$ | Single bond | CH$_2$O | 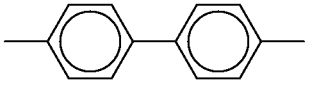 | —C*H(CF$_3$)(CH$_2$)$_5$OC$_2$H$_5$ |
| 52 | " | " | " | " | —C*H(CF$_3$)(CH$_2$)$_4$OCH$_3$ |
| 53 | " | " | " | " | —C*H(CF$_3$)(CH$_2$)$_3$OC$_2$H$_5$ |
| 54 | " | " | " | " | —C*H(CF$_3$)(CH$_2$)$_2$OCH$_3$ |
| 55 | " | " | " | " | —C*H(CF$_3$)(CH$_2$)$_2$OC$_2$H$_5$ |
| 56 | $C_{10}H_{21}$ | COO | CH$_2$O | 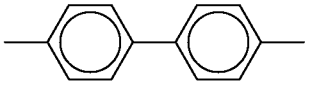 | —C*H(CF$_3$)(CH$_2$)$_5$OC$_2$H$_5$ |
| 57 | " | " | " | " | —C*H(CF$_3$)(CH$_2$)$_4$OCH$_3$ |
| 58 | " | " | " | " | —C*H(CF$_3$)(CH$_2$)$_3$OC$_2$H$_5$ |
| 59 | " | " | " | " | —C*H(CF$_3$)(CH$_2$)$_2$OCH$_3$ |
| 60 | " | " | " | " | —C*H(CF$_3$)(CH$_2$)$_2$OC$_2$H$_5$ |

TABLE 5

| Cpd No. | R¹ | X¹ | Y | A | R¹* |
|---|---|---|---|---|---|
| 61 | $C_{10}H_{21}$ | O | COO | 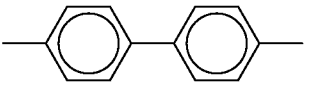 | —C*H(CF$_3$)(CH$_2$)$_5$OC$_2$H$_5$ |
| 62 | " | " | " | " | —C*H(CF$_3$)(CH$_2$)$_4$OCH$_3$ |

TABLE 5-continued

| Cpd No. | $R^1$ | $X^1$ | Y | A | $R^{1*}$ |
|---|---|---|---|---|---|
| 63 | " | " | " | " | —C*H(CF$_3$)(CH$_2$)$_3$OC$_2$H$_5$ |
| 64 | " | " | " | " | —C*H(CF$_3$)(CH$_2$)$_2$OCH$_3$ |
| 65 | " | " | " | " | —C*H(CF$_3$)(CH$_2$)$_2$OC$_2$H$_5$ |
| 66 | C$_{10}$H$_{21}$ | Single bond | COO | biphenyl | —C*H(CF$_3$)(CH$_2$) |
| 67 | " | " | " | " | —C*H(CF$_3$)(CH$_2$)$_4$OCH$_3$ |
| 68 | " | " | " | " | —C*H(CF$_3$)(CH$_2$)$_3$OC$_2$H$_5$ |
| 69 | " | " | " | " | —C*H(CF$_3$)(CH$_2$)$_2$OCH$_3$ |
| 70 | " | " | " | " | —C*H(CF$_3$)(CH$_2$)$_2$OC$_2$H$_5$ |
| 71 | C$_{10}$H$_{21}$ | COO | COO | biphenyl | —C*H(CF$_3$)(CH$_2$)$_5$OC$_2$H$_5$ |
| 72 | " | " | " | " | —C*H(CF$_3$)(CH$_2$)$_4$OCH$_3$ |
| 73 | " | " | " | " | —C*H(CF$_3$)(CH$_2$)$_3$OC$_2$H$_5$ |
| 74 | " | " | " | " | —C*H(CF$_3$)(CH$_2$)$_2$OCH$_3$ |
| 75 | " | " | " | " | —C*H(CF$_3$)(CH$_2$)$_2$OC$_2$H$_5$ |

TABLE 6

| | $R_1$ | $X_1$ | Y | A | $R_1*$ |
|---|---|---|---|---|---|
| 76 | C$_{10}$H$_{21}$ | O | CH$_2$O | phenyl–C≡C– | —C*H(CF$_3$)(CH$_2$)$_5$OC$_2$H$_5$ |
| 77 | " | " | " | " | —C*H(CF$_3$)(CH$_2$)$_4$OCH$_3$ |
| 78 | " | " | " | " | —C*H(CF$_3$)(CH$_2$)$_3$OC$_2$H$_5$ |
| 79 | " | " | " | " | —C*H(CF$_3$)(CH$_2$)$_2$OCH$_3$ |
| 80 | " | " | " | " | —C*H(CF$_3$)(CH$_2$)$_2$OC$_2$H$_5$ |
| 81 | C$_{10}$H$_{21}$ | Single bond | CH$_2$O | phenyl–C≡C– | —C*H(CF$_3$)(CH$_2$)$_5$OC$_2$H$_5$ |
| 82 | " | " | " | " | —C*H(CF$_3$)(CH$_2$)$_4$OCH$_3$ |
| 83 | " | " | " | " | —C*H(CF$_3$)(CH$_2$)$_3$OC$_2$H$_5$ |
| 84 | " | " | " | " | —C*H(CF$_3$)(CH$_2$)$_2$OCH$_3$ |
| 85 | " | " | " | " | —C*H(CF$_3$)(CH$_2$)$_2$OC$_2$H$_5$ |
| 86 | C$_{10}$H$_{21}$ | COO | CH$_2$O | phenyl–C≡C– | —C*H(CF$_3$)(CH$_2$)$_5$OC$_2$H$_5$ |
| 87 | " | " | " | " | —C*H(CF$_3$)(CH$_2$)$_4$OCH$_3$ |
| 88 | " | " | " | " | —C*H(CF$_3$)(CH$_2$)$_3$OC$_2$H$_5$ |
| 89 | " | " | " | " | —C*H(CF$_3$)(CH$_2$)$_2$OCH$_3$ |
| 90 | " | " | " | " | —C*H(CF$_3$)(CH$_2$)$_2$OC$_2$H$_5$ |

TABLE 7

| Cpd. No. | R₁ | X₁ | Y | A | R₁* |
|---|---|---|---|---|---|
| 91 | $C_{10}H_{21}$ | O | COO | –⟨C₆H₄⟩–C≡C– | —C*H(CF₃)(CH₂)₅OC₂H₅ |
| 92 | " | " | " | " | —C*H(CF₃)(CH₂)₄OCH₃ |
| 93 | " | " | " | " | —C*H(CF₃)(CH₂)₃OC₂H₅ |
| 94 | " | " | " | " | —C*H(CF₃)(CH₂)₂OCH₃ |
| 95 | " | " | " | " | —C*H(CF₃)(CH₂)₂OC₂H₅ |
| 96 | $C_{10}H_{21}$ | Single bond | COO | –⟨C₆H₄⟩–C≡C– | —C*H(CF₃)(CH₂)₅OC₂H₅ |
| 97 | " | " | " | " | —C*H(CF₃)(CH₂)₄OCH₃ |
| 98 | " | " | " | " | —C*H(CF₃)(CH₂)₃OC₂H₅ |
| 99 | " | " | " | " | —C*H(CF₃)(CH₂)₂OCH₃ |
| 100 | " | " | " | " | —C*H(CF₃)(CH₂)₂OC₂H₅ |
| 101 | $C_{10}H_{21}$ | COO | COO | –⟨C₆H₄⟩–C≡C– | —C*H(CF₃)(CH₂)₅OC₂H₅ |
| 102 | " | " | " | " | —C*H(CF₃)(CH₂)₄OCH₃ |
| 103 | " | " | " | " | —C*H(CF₃)(CH₂)₃OC₂H₅ |
| 104 | " | " | " | " | —C*H(CF₃)(CH₂)₂OCH₃ |
| 105 | " | " | " | " | —C*H(CF₃)(CH₂)₂OC₂H₅ |

TABLE 8

| Cpd No. | R₁ | X₁ | Y | A | R₁I |
|---|---|---|---|---|---|
| 106 | $C_{10}H_{21}$ | O | CH₂O | –⟨C₆H₄⟩–C≡C– | —C*H(CF₃)(CH₂)₅OC₂H₅ |
| 107 | " | " | " | " | —C*H(CF₃)(CH₂)₄OCH₃ |
| 108 | " | " | " | " | —C*H(CF₃)(CH₂)₃OC₂H₅ |
| 109 | " | " | " | " | —C*H(CF₃)(CH₂)₂OCH₃ |
| 110 | " | " | " | " | —C*H(CF₃)(CH₂)₂OC₂H₅ |
| 111 | $C_{10}H_{21}$ | Single bond | CH₂O | –⟨C₆H₄⟩–C≡C– | —C*H(CF₃)(CH₂)₅OC₂H₅ |
| 112 | " | " | " | " | —C*H(CF₃)(CH₂)₄OCH₃ |
| 113 | " | " | " | " | —C*H(CF₃)(CH₂)₃OC₂H₅ |
| 114 | " | " | " | " | —C*H(CF₃)(CH₂)₂OCH₃ |
| 115 | " | " | " | " | —C*H(CF₃)(CH₂)₂OC₂H₅ |
| 116 | $C_{10}H_{21}$ | COO | CH₂O | –⟨C₆H₄⟩–C≡C– | —C*H(CF₃)(CH₂)₅OC₂H₅ |
| 117 | " | " | " | " | —C*H(CF₃)(CH₂)₄OCH₃ |
| 118 | " | " | " | " | —C*H(CF₃)(CH₂)₃OC₂H₅ |
| 119 | " | " | " | " | —C*H(CF₃)(CH₂)₂OCH₃ |
| 120 | " | " | " | " | —C*H(CF₃)(CH₂)₂OC₂H₅ |

TABLE 9

| Cpd. No. | $R_1$ | $X_1$ | Y | A | $R_1*$ |
|---|---|---|---|---|---|
| 121 | $C_{10}H_{21}$ | O | COO | –C₆H₄–C≡C– | —C*H(CF$_3$)(CH$_2$)$_5$OC$_2$H$_5$ |
| 122 | " | " | " | " | —C*H(CF$_3$)(CH$_2$)$_4$OCH$_3$ |
| 123 | " | " | " | " | —C*H(CF$_3$)(CH$_2$)$_3$OC$_2$H$_5$ |
| 124 | " | " | " | " | —C*H(CF$_3$)(CH$_2$)$_2$OCH$_3$ |
| 125 | " | " | " | " | —C*H(CF$_3$)(CH$_2$)$_2$OC$_2$H$_5$ |
| 126 | $C_{10}H_{21}$ | Single bond | COO | –C₆H₄–C≡C– | —C*H(CF$_3$)(CH$_2$)$_5$OC$_2$H$_5$ |
| 127 | " | " | " | " | —C*H(CF$_3$)(CH$_2$)$_4$OCH$_3$ |
| 128 | " | " | " | " | —C*H(CF$_3$)(CH$_2$)$_3$OC$_2$H$_5$ |
| 129 | " | " | " | " | —C*H(CF$_3$)(CH$_2$)$_2$OCH$_3$ |
| 130 | " | " | " | " | —C*H(CF$_3$)(CH$_2$)$_2$OC$_2$H$_5$ |
| 131 | $C_{10}H_{21}$ | COO | COO | –C₆H₄–C≡C– | —C*H(CF$_3$)(CH$_2$)$_5$OC$_2$H$_5$ |
| 132 | " | " | " | " | —C*H(CF$_3$)(CH$_2$)$_4$OCH$_3$ |
| 133 | " | " | " | " | —C*H(CF$_3$)(CH$_2$)$_3$OC$_2$H$_5$ |
| 134 | " | " | " | " | —C*H(CF$_3$)(CH$_2$)$_2$OCH$_3$ |
| 135 | " | " | " | " | —C*H(CF$_3$)(CH$_2$)$_2$OC$_2$H$_5$ |

TABLE 10

| Cpd No. | $R_1$ | $X_1$ | Y | A | $R_1I$ |
|---|---|---|---|---|---|
| 136 | $C_{10}H_{21}$ | O | CH$_2$O | –C₆H₄–C≡C– | —C*H(CF$_3$)(CH$_2$)$_5$OC$_2$H$_5$ |
| 137 | " | " | " | " | —C*H(CF$_3$)(CH$_2$)$_4$OCH$_3$ |
| 138 | " | " | " | " | —C*H(CF$_3$)(CH$_2$)$_3$OC$_2$H$_5$ |
| 139 | " | " | " | " | —C*H(CF$_3$)(CH$_2$)$_2$OCH$_3$ |
| 140 | " | " | " | " | —C*H(CF$_3$)(CH$_2$)$_2$OC$_2$H$_5$ |
| 141 | $C_{10}H_{21}$ | Single bond | CH$_2$O | –C₆H₄–C≡C– | —C*H(CF$_3$)(CH$_2$)$_5$OC$_2$H$_5$ |
| 142 | " | " | " | " | —C*H(CF$_3$)(CH$_2$)$_4$OCH$_3$ |
| 143 | " | " | " | " | —C*H(CF$_3$)(CH$_2$)$_3$OC$_2$H$_5$ |
| 144 | " | " | " | " | —C*H(CF$_3$)(CH$_2$)$_2$OCH$_3$ |
| 145 | " | " | " | " | —C*H(CF$_3$)(CH$_2$)$_2$OC$_2$H$_5$ |
| 146 | $C_{10}H_{21}$ | COO | CH$_2$O | –C₆H₄–C≡C– | —C*H(CF$_3$)(CH$_2$)$_5$OC$_2$H$_5$ |
| 147 | " | " | " | " | —C*H(CF$_3$)(CH$_2$)$_4$OCH$_3$ |
| 148 | " | " | " | " | —C*H(CF$_3$)(CH$_2$)$_3$OC$_2$H$_5$ |
| 149 | " | " | " | " | —C*H(CF$_3$)(CH$_2$)$_2$OCH$_3$ |
| 150 | " | " | " | " | —C*H(CF$_3$)(CH$_2$)$_2$OC$_2$H$_5$ |

The tetralin compound represented by the formula [I] may be synthesized in accordance with the following synthesis route. In the following synthesis route, R* denotes $R^{1*}$ shown in the formula [I], and $R^0$, $R^1$ and $R^2$ are each independently an alkyl group of 1–20 carbon atoms or an alkoxy group of 1–20 carbon atoms.

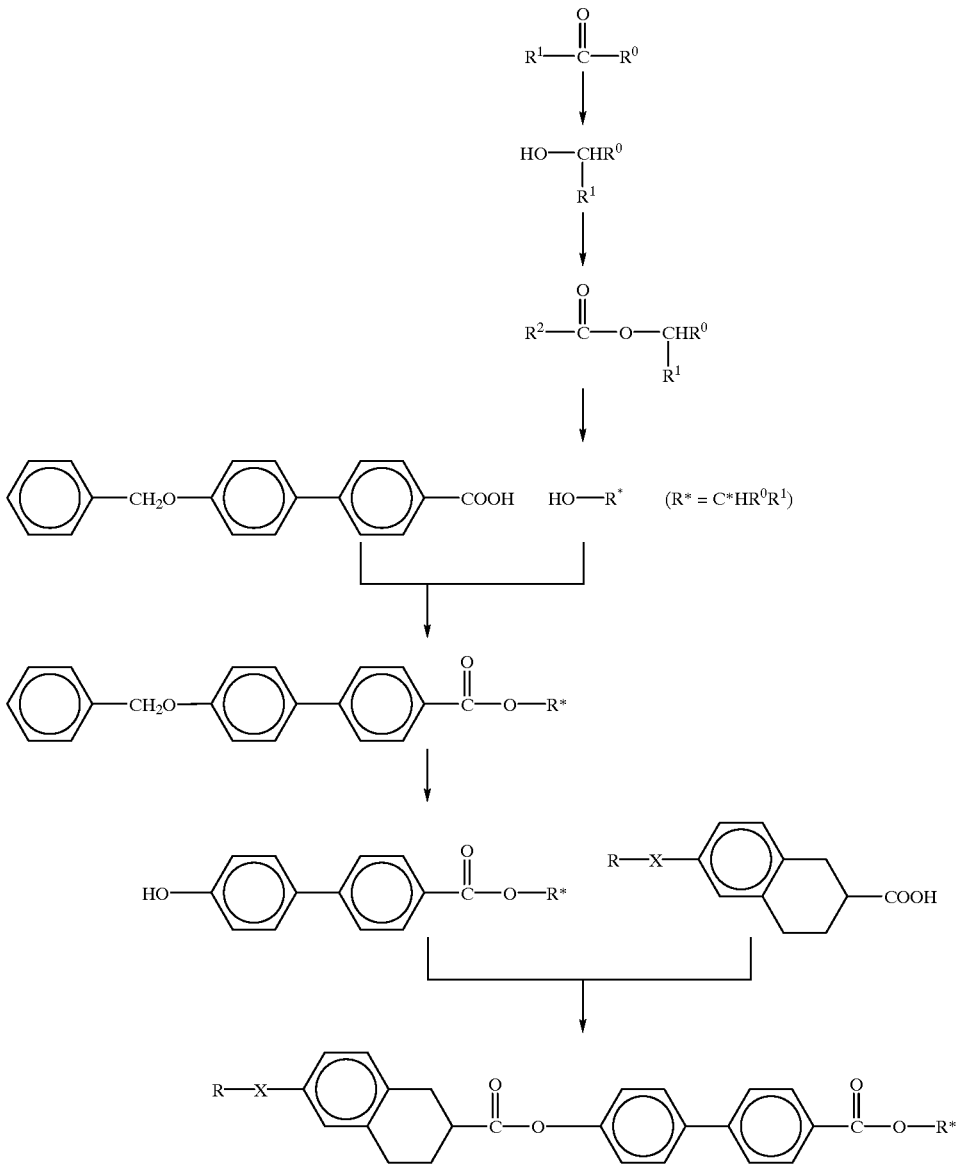

The process for manufacturing the tetralin compound to be used as the liquid crystal material of the invention is explained in further details as follows.

a) At the outset, for example, a ketone containing a trifluoromethyl group ($R^1$—CO—$R^0$) is reduced with a reducing agent, and, thus is obtained a fluorine-containing alcohol (HO-$CHR^1R^0$). As to the reducing agent to be used in this case, there is no limitation so long as it is capable of converting a carbonyl group into a hydroxy group. Examples of such reducing agent include sodium borohydride and lithium aluminum hydride. It is preferable to use diethyl ether, tetrahydrofuran, etc. as the solvent to be utilized in the reaction when lithium aluminum hydride is used as the reducing agent. The reaction temperature is adequately adjusted in accordance with the kind of ketone containing a trifluoromethyl group and the reducing agent employed, and there is no particular limitation as to the reaction temperature. Nevertheless, room temperature or a temperature in its vicinity is preferable.

Subsequently, the fluorine-containing alcohol obtained in accordance with the aforementioned procedure (HO—$CHR^1R^0$) is esterified in accordance with the conventional process, and thus is obtained an esterification product ($R^2$—COO—$CHR^1R^0$). It is preferable to use a carboxylic acid chloride(for example, acetyl chloride, propionyl chloride, butyryl chloride, etc.) as the esterifying agent.

Thereupon, the esterification product thus obtained ($R^2$—COO—$CHR^1R^0$) is a racemic modification in which equal quantities of R-form and S-form are mixed together, then the esterification product is subjected to asymmetric hydrolysis, using a hydrolase (for example, lipase-P, lipase-MY, lipase-OF, cellulase, etc.), and thus is obtained an optically active alcohol (R-alcohol or S-alcohol; HO—$R^*$:$R^*$=$CHR^1R^0$). The dosage of this hydrolase is 500–20,000 units per 1 mmol of the raw material racemic ester, preferably 1000–5000 units. Such hydrolysis is carried out usually in water or in a mixed solvent prepared by mixing a water-soluble solvent like methanol, ethanol, etc. with water. The quantity of the racemic ester to be used as a raw material is so adjusted that it will be contained in the solvent by a concentration of 1–40 percent by weight, or preferably 3–30 percent by weight.

The pH of the liquid in which the said asymmetric hydrolysis reaction is carried out is preferably adjusted to within a range of 6–8, and the reaction temperature is preferably maintained in a range of 10–40° C.

b) 4'-benzyloxy-4-biphenylcarboxylic acid is obtained by subjecting 4'-hydroxy-4-biphenylcarboxylic acid and a benzyl halide to a condensation reaction in the presence of a salt like potassium hydroxide.

Thereupon, 4'-benzyloxy-4-biphenylcarboxylic acid ester is obtained by causing the optically active alcohol obtained in accordance with the said process to react with 4'-benzyloxy-4-biphenylcarboxylic acid, using a dehydrating-condensation agent such as N,N'-dicyclohexylcarbodiimide.

By adding 4'-benzyloxy-4-biphenylcarboxylic acid ester thereby obtained to a solvent like tetrahydrofuran and reducing it with hydrogen in the presence of a reducing catalyst such as palladium/carbon, there is obtained 4'-hydroxy-4-biphenylcarboxylic acid ester.

c) 1,2,3,4-tetrahydro-6-alkoxy-2-naphthalenecarboxylic acid is obtained by refluxing a mixture of, for example, 6-alkoxy-2-naphthalenecarboxylic acid and, 1,2-diethoxy ethane in the presence of metallic sodium with isoamyl alcohol continuously dropwise added.

4'-(1,2,3,4-tetrahydro-6-alkoxy-2-naphthalenecarbonyloxy)-4-biphenylcarboxylic acid ester, which is the tetralin compound of the invention, can be obtained by causing 1,2,3,4-tetrahydro-6-alkoxy-2-naphthalenecarboxylic acid to react with 4'-hydroxy-4-biphenylcarboxylic acid ester obtained in the aforesaid process, using a dehydrating-condensation agent like N,N'-dicyclohexylcarbodiimide.

d) The said 4'-(1,2,3,4-tetrahydro-6-alkoxy-2-naphthalenecarbonyloxy)-4-biphenylcarboxylic acid ester can be also synthesized in accordance with the following synthesis route.

Namely, 1,2,3,4-tetrahydro-6-alkoxy-2-naphthalenecarboxylic acid is subjected to a dehydration reaction with 4'-hydroxy-4-biphenylcarboxylic acid benzyl ester, and thus is obtained 4'-(1,2,3,4-tetrahydo-6-alkoxy-2-naphthalenecarbonyloxy)-4-biphenylcarboxylic acid benzyl ester. Thereupon, the reaction product is debenzylated by reduction with hydrogen, and thus is obtained 4-(1,2,3,4-tetrahydo-6-alkoxy-2-naphthalenecarbonyloxy)-4-biphenylcarboxylic acid. It is by way of reacting this reaction product with an optically active alcohol that 4'-(1,2,3,4-6-alkoxy-2-naphthalenecarbonyloxy)-4-biphenylcarboxylic acid ester, which is the said tetralin compound, can be obtained.

The aforementioned method represents only one example of the method for manufacturing the tetralin compound to be used as a liquid crystal material of the present invention, and hence the tetralin compound used as the liquid crystal material in the invention is not limited to the tetralin compound obtained solely in accordance with the said method.

The liquid crystal compound of the invention is any of such liquid crystal material comprising the tetralin compound represented by the formula [I].

The liquid crystal material comprising the tetralin compound represented by the formula [I] which is obtained in accordance with the aforesaid method can be used as a ferroelectric liquid crystal compound or an antiferroelectric compound.

Liquid Crystal Composition

The liquid crystal composition of the invention includes the tetralin compound represented by the formula [I]. Either a single kind or 2 or more kinds of the tetralin compound represented by the formula [I] may be used.

Among the tetralin compounds represented by the formula [I] there are some compounds whose lower limit temperatures at which the smectic phase appears are higher than room temperature, while there are other compounds which do not exhibit the smectic phase at all. Even both of those components are made capable of providing a liquid crystal element which exhibits the smectic phase at a low lower limit temperature, for example, over a wide temperature range including room temperature when the tetralin compound represented by the formula [I] is mixed as a main ingredient or as an assistant with another liquid crystal material (which may be a tetralin compound represented by the formula [I] which is of a different kind from the main ingredient). Particularly, in case that the tetralin compound represented by the formula [I] does not exhibit the smectic phase, it is preferable that the tetralin compound represented by the formula [I] is mixed as an assistant with another liquid crystal material, which exhibits the smectic phase. Examples of another liquid crystal material, which exhibits the smectic phase include ferroelectric liquid crystal material and antiferroelectric liquid crystal material.

Further particularly, among the ferroelectric liquid crystal compounds usable with the compound represented by the formula [I] of the invention, there is no limitation and the following examples may be cited as preferable compounds.

Esters including 2 aromatic rings such as

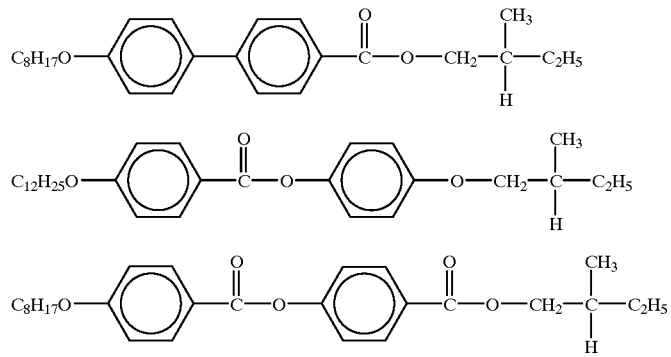

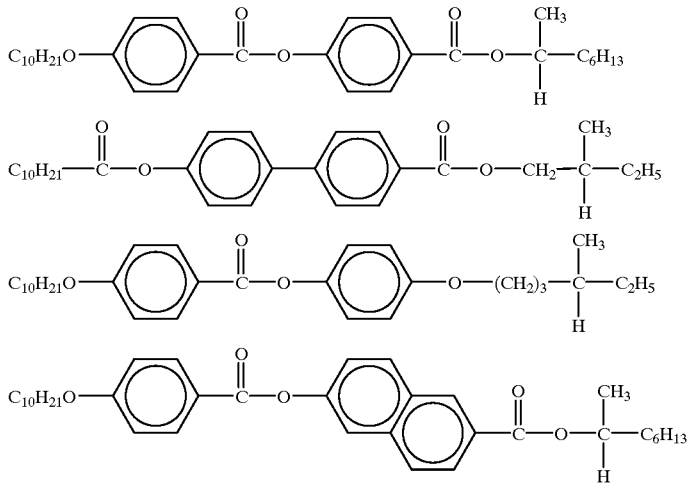

and pyrimidinephenyl compounds such as

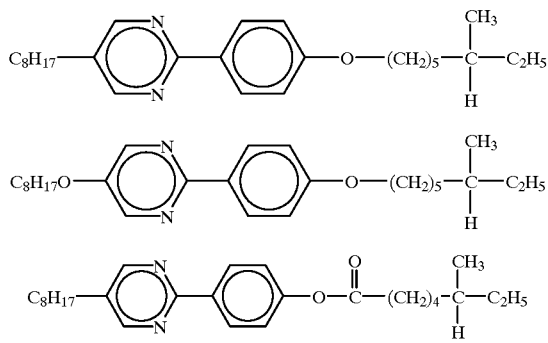

From among those antiferroelectric liquid crystal compounds usable with a compound represented by the formula [I] of the invention, there are cited as preferable examples antiferroelectric liquid crystal compounds containing a compound represented by the following formula (III).

[III]

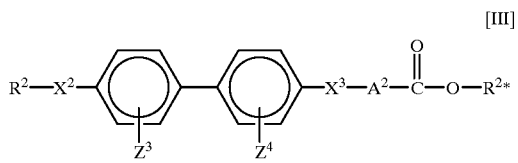

wherein $R^2$ is an alkyl group or a polyfluoroalkyl group of 3–20 carbon atoms, and a single or two or more mutually nonadjacent —$CH_2$— or -$CF_2$— in those groups may be substituted with —O—.

$A^2$ represents a group selected from the group consisting of

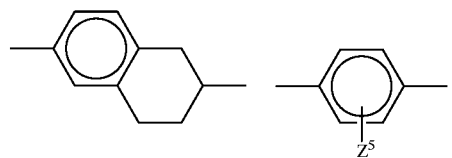

$Z^3$, $Z^4$ and $Z^5$ are each independently a hydrogen atom or a fluorine atom.

In the formula [III], $X^2$ is —COO—, —O—, or a single bond; $X^3$ is —COO— or —$CH_2O$—; R2* is an optically active group represented by the following formula [IV] (wherein when V is $CF_3$, p≠0 and r≠0, and p=0 and r=0; and when V is —$CH_3$ p=0 and r=0).

$$—C^*HV—(CH_2)_r—(O)_p—C_qH_{2q+1} \qquad [IV]$$

(wherein r is preferably 0 to 10 and q is preferably 0 to 10.)

The liquid crystal composition of the invention can be manufactured by mixing the tetralin compound represented by the formula [I] and optionally the compound represented by the formula [III] with other liquid crystal materials and additive as desired.

The blending ratio of the tetralin compound represented by the formula [I] in the liquid crystal compound of the invention may be optionally determined in consideration of intended properties of the liquid crystal composition to be obtained. The composition of the invention contains the tetralin compound represented by the formula [I] by a concentration in the total volume of the liquid crystal components constituting the liquid crystal composition usually in a range of 5–99 mole %, preferably 10–75 mole %.

In the liquid crystal composition of the invention, additives which are incorporated into conventional liquid crystal compositions, such as a conductivity-imparting agent and a life-extending agent, may be included in addition to the liquid crystal materials of the invention.

The liquid crystal composition used in the invention may be manufactured by mixing therewith the tetralin compound cited above and optionally such other liquid crystal material and additives as desired.

Since the liquid crystal composition containing the above-mentioned liquid crystal material demonstrates an optical switching phenomenon when a voltage is applied a display device affording a high response speed can be prepared, utilizing this phenomenon. With regard to the element utilizing such phenomenon or the method of driving such element in the invention, reference may be made to Japanese Laid-open Patent Application No. Sho56(81)-107216 and Japanese Laid-open Patent Application No. Sho59(84)-118744.

There is provided by the invention a novel liquid crystal material for which a tetralin compound is used.

Such tetralin compound is optically active and exhibits the smectic phase over a wide temperature range and may be utilized as a ferroelectric liquid crystal compound or an antiferroelectrical liquid crystal compound.

The response speed can be controlled by mixing with the liquid crystal material of the invention a same kind of and/or a different kind of liquid crystal material without marring antiferroelectric characteristics or ferroelectric characteristics of the liquid crystal material of the invention.

Accordingly, liquid crystal elements, etc. having a high response speed over a wide temperature range can be obtained by using such liquid crystal material.

Moreover, the operating time can be shortened substantially with the liquid crystal display devices, incorporating such element. Electric power consumption can be reduced with such display device. Additionally, a high contrast can be achieved, as a very large tilted molecular orientation, namely, a tilt angle, can be secured and liquid crystal orientation, namely, alignability, can be enhanced, and consequentially a high contrast can be achieved. Furthermore, a stable contrast can be achieved.

EXAMPLES

The present invention is further described below with reference to examples, but it should be construed that the invention is in no way limited to those examples. In the examples, R and S mean R-form and S-form of an optically active compound, respectively. Determination of the phase transition temperature and identification of the phase in those examples were carried out in accordance with a differential scanning calorimetry (DSC) method and by polarimicroscopic observation of liquid crystal elements fabricated as specimens to verify the response in the electric field.

In the invention the threshold voltage and the response time of the liquid crystal composition in a liquid crystal cell were determined in accordance with the following procedures, respectively.

Threshold voltage

Figure 8:
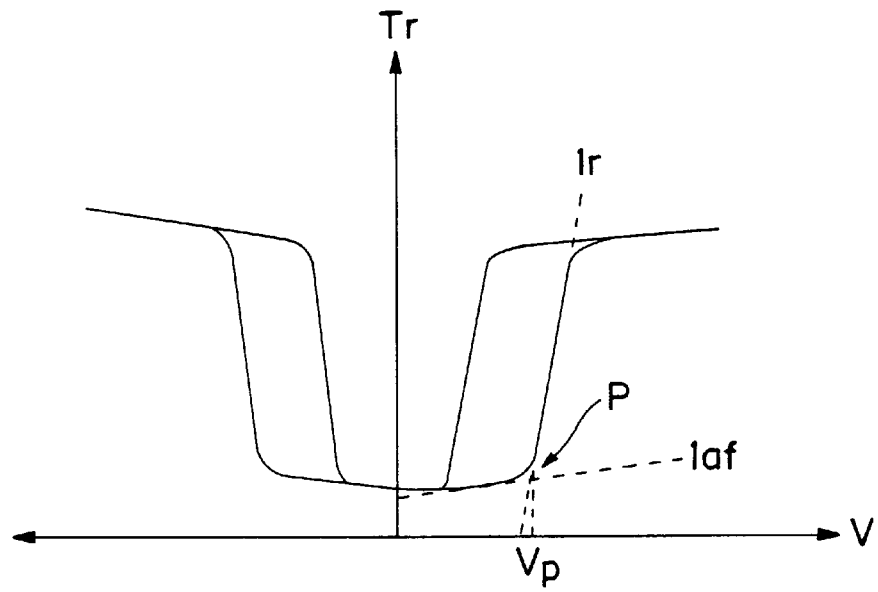
FIG. 8 illustrates a procedure of determining the threshold voltage of a liquid crystal composition in a liquid crystal cell of the invention.

A triangular wave voltage (frequency:0.01 Hz and peak voltage:30 V/2 μm) was applied to a liquid crystal cell in a liquid crystal element, and the light transmission (Tr) of the liquid crystal element was monitored. When the voltage (V) applied to the liquid crystal cell was increased from zero in the positive direction, a phase transition occurred from the antiferroelectric state to the ferroelectric state, and the light transmission of the liquid crystal element increased. A V-Tr curve is shown in FIG. 8. In FIG. 8, the point of intersection (P) where the tangent line (Ir) of this V-Tr cure intersects the V-Tr curve in the antiferroelelctric area was pin-pointed and the voltage (Vp) at this intersection (P) was recorded as the threshold voltage.

Response time

Figure 9:
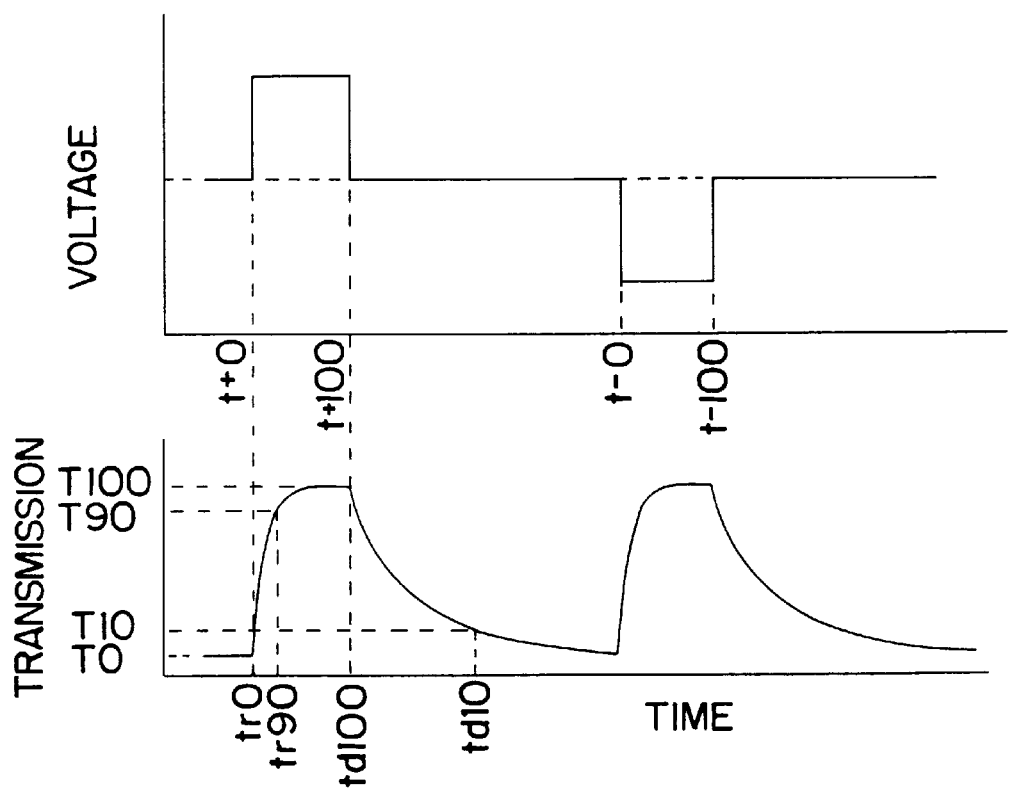
FIG. 9 illustrates a procedure of determining the response time of a liquid crystal composition in a liquid crystal cell of the invention.

A pulse voltage (amplitude of voltage pulse: 5 msec; pulse interval: 500 msec) was applied to a liquid crystal cell in a liquid crystal element, and the light transmission of the liquid crystal element was monitored. FIG. 9 shows an exemplified relationship between the applied driving voltage pulse and the level of transmission as related to the rise ($t_r$) and decay ($t_{decay}$) times. The response time was evaluated in accordance with the following formula on the basis of variances in the light transmission.

Response time=$Tr90-Tr0$

Example 1

Synthesis of 4'-(6-decyloxy-1,2,3,4-tetrahydro-2-naphthalenecarbonyloxy)-4-biphenylcarboxylic acid (R)-1-trifluoromethyl-3-methoxypropyl ester [Exemplified Compound (4)]

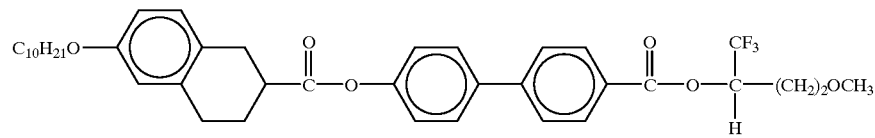

First Stage

To a mixture of 3.86 g (11.8 mmol) of 6-decyloxy-2-naphthalenecarboxylic acid and 130 ml of 1,2-diethoxyethane was added with stirring, 3.0 g (130 mmol) of metallic sodium at 120° C. in a nitrogen atmosphere, and the resulting mixture was heated to a reflux temperature.

To this mixture was dropwise added 10 g (114 mmol) of isoamyl alcohol over 1 hour, and they were reacted with each other for 11 hours under reflux. After cooling of the reaction system to room temperature, to the reaction mixture was added ethanol to convert the remaining metallic sodium into sodium alcoholate. Then, the reaction mixture was made acidic using 20% hydrochloric acid.

To the reaction mixture was added 100 ml of water, then the resulting organic phase was separated from the mixture, and the organic phase was washed with water. The organic phase was concentrated under a reduced pressure to obtain 4.25 g of a solid. By recrystalizing this solid with toluene there was obtained 2.95 g of 6-decyloxy-1,2,3,4-tetrahydro-2-naphthalenecarboxylic acid. The yield was 75%.

Second Stage

A mixture of 3.32 g (10 mmol) of the 6-decyloxy-1,2,3,4-tetrahydro-2-naphthalenecarboxylic acid obtained in the first stage, 2.14 g (10 mmol) of 4'-hydroxy-4-biphenylcarboxylic acid, and 0.12 g (1 mmol) of 4-N,N-dimethylaminopyridine (DMAP) was added to 50 ml of methylene chloride. To this mixture was dropwise added 15 ml of methylene chloride solution of 2.27 g (11 mmol) of N,N'-dicyclohexylcarbodiimide (DCC), and thereupon 20 ml of methylene chloride was further added to the mixture. The resulting reaction mixture was stirred for 6 hours at room temperature. The reaction mixture was filtered to obtain a solid, and the solid thus obtained was dissolved in tetrahydrofuran (THF). The dissolvable portion was separated, and the solvent was removed by fractionation. Thereupon, the residue was recrystallized with a mixed solvent of THF and methylene chloride to obtain 1.92 g of 4'-(1,2,3,4-tetrahydro-6-decyloxy-2-naphthalenecarbonyloxy)-4-biphenylcarboxylic acid. The yield was 36%.

Third Stage

To a mixture of 0.35 g (0.66 mmol) of 4'-(1,2,3,4-tetrahydro-6-decyloxy-2-naphthalenecarbonyloxy)-4- biphenylcarboxylic acid, 0.11 g (0.7 mmol) of (R)-1-trifluoromethyl-3-methoxypropyl alcohol, 0.018 g (0.15 mmol) of DMAP and 20 mmol of methylene chloride was dropwise added with stirring 10 ml of a methylene chloride solution of 0.19 g (0.92 mmol) of DDC over 2 hours at room temperature, and they were reacted with each other for 48 hours at room temperature.

This reaction mixture was filtered, and the obtained filtrate was concentrated, and by purifying the resulting concentrate using column chromatography 0.23 g of a colorless semisolid was obtained.

This semisolid had an M/e value in FD-mass spectrum of 668.

A $^1$H-NMR spectrum of this compound is shown in FIG. 1.

As the result of analysis of these spectra, the compound was identified as 4'-(6-decyloxy-1,2,3,4-tetrahydro-2-naphthalenecarbonyloxy)-4-biphenylcarboxylic acid (R)-1-trifluoromethyl-3-methoxypropyl ester, the target material [Exemplified Compound (4)]. The yield was 52%.

The phase transition temperatures of the liquid crystal compound are set forth in Table 11.

TABLE 11

| | Cry | | SmC$_A$* | | SmC* | SmA | | Iso |
|---|---|---|---|---|---|---|---|---|
| Example 1 | • | 58 | • | (45) | — | • | 103 | • |

In Tables 11 through Table 24 in Examples, Cry, SmC$_A$*, SmC*, SmA, and Iso each denote a crystal phase, an antiferroelectric phase, a ferroelectric phase, a smectic A phase and an isotropic liquid phase, respectively. Further, the symbol "•" means that the compound can be in the corresponding phase, the numeral denotes a phase transition temperature between the phases indicated and the symbol "–" means that the compound cannot be in the phase.

Example 2

Synthesis of 4'-(6-decyloxy-1,2, 3,4-tetrahydro-2-naphthalenecarbonyloxy)-3-fluoro-4-biphenylcarboxylic acid (R)-1-trifluoromethyl-3-methoxypropyl ester [Exemplified Compound (34)]

Second Stage

A mixture of 3.85 g (16.9 mmol) of the 4'-methoxy-3-fluoro-4-cyanobiphenyl obtained in the first stage and 19.5 ml (169 mmol) of a 47% aqueous solution of hydrogen bromide was added to 80 ml of acetic acid, and the resulting mixture was heated under reflux for 10 hours. After cooling of the reaction system, to the reaction mixture was added a copious amount of water to precipitate a solid. After dissolving the obtained solid in acetone and removing an insoluble matter, hexane was added to the acetone solution to obtain 2.40 g (10.3 mmol) of 4'-hydroxy-3-fluoro-4-biphenylcarboxylic acid in a white crystalline form. The yield was 61%.

Third Stage

A mixture of 2.39 g (10.3 mmol) of the 4'-hydroxy-3-fluoro-4-biphenylcarboxylic acid obtained in the second stage, 3.89 g (36.1 mmol) of benzyl alcohol, and 0.038 g (0.155 mmol) of dibutyltin oxide was heated under reflux for 6 hours. After cooling of the reaction system, the reaction mixture was dissolved in acetone, and by way of removing an insoluble matter, the solution was concentrated. By means of column purification and recrystalization, 2.50 g (7.76 mmol) of 4'-decyloxy-3-fluoro-4-biphenylcarboxylic acid was obtained as a whitish pale yellow needle crystal matter. The yield was 75%.

Fourth Stage

To a mixture of 2.42 g (7.5 mmol) of 4'-decyloxy-3-fluoro-4-biphenylcarboxylic acid obtained in the third stage, 2.49 g (7.5 mmol) of the 6-decyloxy-1,2,3,4-tetrahydro-2-naphthalenecarboxylic acid obtained in the first stage of Example 1, 0.092 g (0.75 mmol) of DMAP and 30 ml of methylene chloride there was dropwise added with stirring 15 ml of a methylene chloride solution of 1.70 g (8.25 mmol) of DCC over 4 hours at room temperature. The resulting mixture was further caused to undergo the reaction for 20 hours at room temperature. The reaction mixture was filtered and the filtrate thus obtained was concentrated. The resulting concentrate was separated by means of column chromatography to obtain 4.19 g (6.59 mmol) of 4'-(6-decyloxy-1,2,3,4-tetrahydro-2-naphthalenecarbonyloxy)-3-fluoro-4-biphenylcarboxylic acid benzyl ester as a white solid. The yield was 88%.

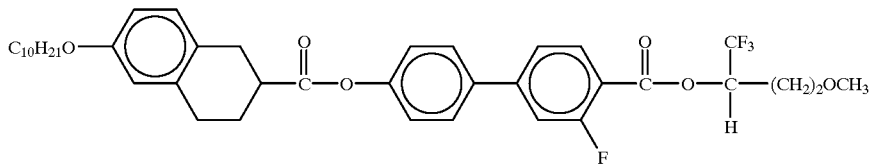

First Stage

A mixture of 1.52 g (10 mmol) of 4-methoxybenzeneboron acid, 2.00 g (10 mmol) of 4-bromo-2-fluorobenzonitryl, 50 ml of 1,2-dimethoxyethane, 0.23 g (0.2 mmol) of tetrakis (triphenylphosphine) palladium and 4.14 g (30 mmol) of potassium carbonate was refluxed for 5 hours. After cooling of the reaction system, to the reaction mixture was added 70 ml of water, and the resulting white precipitate was filtered out. The white precipitate was washed with water/hexane and was dissolved in hexane. After removing the insoluble matter by filtration, the solution was recrystallized with an acetone/hexane mixed solvent to obtain 2.07 g (9.12 mmol) of 4'-methoxy-3-fluoro-4-cyanobiphenyl in a white crystalline form. The yield was 91%.

Fifth Stage

Into a mixture of 4.19 g (6.59 mmol) of the 4'-(6-decyloxy-1,2,3,4-tetrahydro-2-naphthalenecarbonyloxy)-3-fluoro-4-biphenylcarboxylic acid benzyl ester obtained in the fourth stage and 50 ml of a THF solution containing 0.838 g of 5% palladium/carbon was blown hydrogen gas with stirring for 3 days. The reaction mixture was filtered, and the filtrate thus obtained was concentrated to obtain 3.48 g (6.37 mmol) of 4'-(6-decyloxy-1,2,3,4-tetrahydro-2-naphthalenecarbonyloxy)-3-fluoro-4-biphenyl carboxylic acid as a white solid.

Sixth Stage

To a mixture of 0.66 g (1.2 mmol) of the 4'-(6-decyloxy-1,2,3,4-tetrahydro-2-naphthalenecarbonyloxy )-3-fluoro-4- biphenyl carboxylic acid obtained in the fifth stage, 0.19 g (1.2 mmol) of Chem29 and 5 ml of methylene chloride containing 0.02 g (0.16 mmol) of DMAP was dropwise added with stirring 5 ml of a methylene chloride solution of 29 g (1.4 mmol) of DCC at room temperature. The reaction was further carried out at room temperature for 48 hours. The reaction mixture was filtered and the filtrate thus obtained was concentrated. By purifying the concentrate using column chromatography, 0.60 g of a colorless semisolid was obtained.

This semisolid had an M/e value in FD-mass spectrum of 686.

Figure 2:
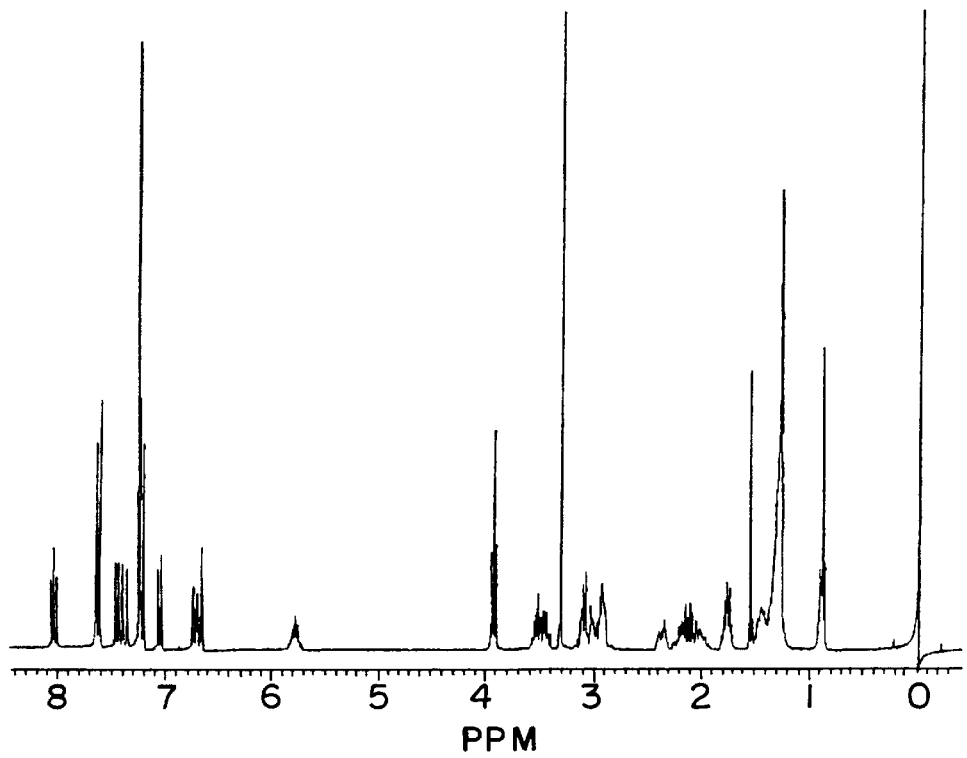
FIG. 2 shows a $^1$H-NMR spectrum of 4'-(6-decyloxy-1,2,3,4-tetrahydro-2-naphthalenecarbonyloxy)-3-fluoro-4-biphenylcarboxylic acid (R)-1-trifluoromethyl-3-methoxypropyl ester.

A $^1$H-NMR spectrum of this compound is shown FIG. 2.

From the analysis of these spectra, this compound was identified as 4'-(6-decyloxy-1,2,3,4-tetrahydro-2-naphthalenecarbonyloxy)-3-fluoro-4-biphenylcarboxylic acid (R)-1-trifluoromethyl-3-methoxypropyl ester, the target material [Exemplified Compound (34)]. The yield was 73%.

The phase transition temperatures of this liquid crystal compound are set forth in Table 12.

stirring 5 ml of a methylene chloride solution of 0.29 g (1.4 mmol) of DCC at room temperature over 2 hours. The resulting mixture was further stirred at room temperature for 48 hours.

The reaction mixture was filtered and the filtrate thus obtained was concentrated. By purifying the concentrate using column chromatography, 0.54 g of a white semisolid was obtained.

This semisolid had an M/e value in FD-mass spectrum of 714.

Figure 3:
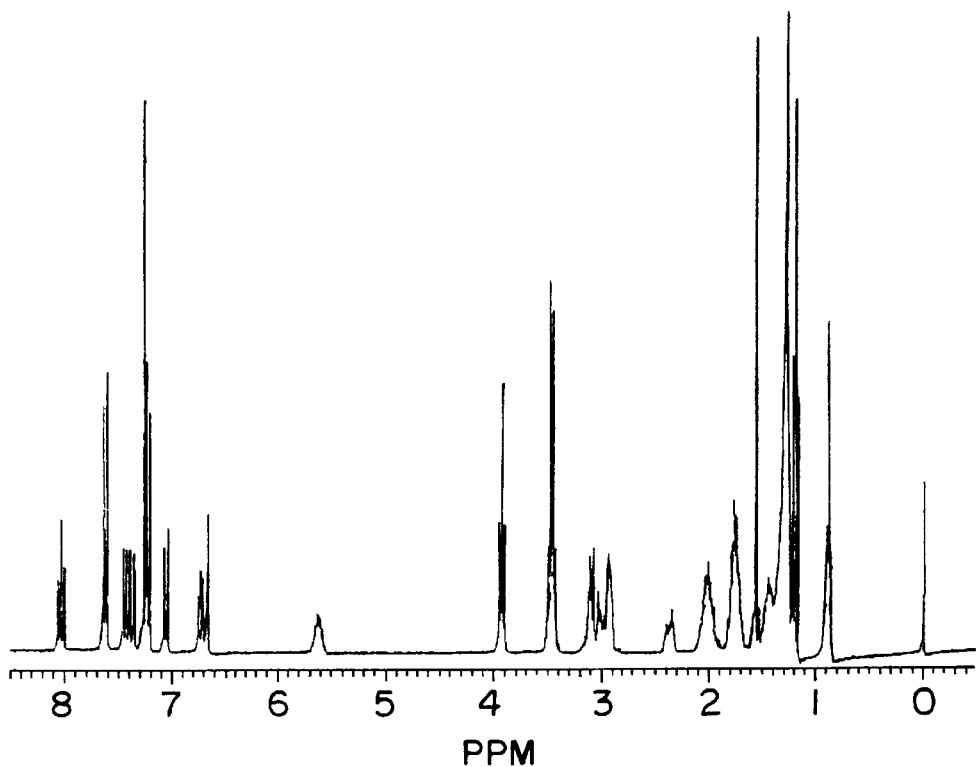
FIG. 3 shows a $^1$H-NMR spectrum of 4'-(6-decyloxy-1,2,3,4-tetrahydro-2-naphthalenecarbonyloxy)-3-fluoro-4-biphenylcarboxylic acid (R)-1-trifluoromethyl-4-ethoxypropyl ester.

A $^1$H-NMR spectrum of this compound is shown in FIG. 3.

From the analysis of these spectra, this compound was identified as 4'-(6-decyloxy-1,2,3,4-tetrahydro-2-naphthalenecarbonyloxy)-3-fluoro-4-biphenylcarboxylic acid (R)-1-trifluoromethyl-4-ethoxypropyl ester, the target material [Exemplified Compound (33)]. The yield was 63%.

The phase transition temperatures of this liquid crystal compound are set forth in Table 13.

TABLE 12

| | Cry | | SmC$_A$* | | SmC* | | SmA | | Iso |
|---|---|---|---|---|---|---|---|---|---|
| Example 2 | • | 40 | • | (40) | • | 64 | • | 87 | • |

TABLE 13

| | Cry | | SmC$_A$. | SmC* | | SmA | | Iso |
|---|---|---|---|---|---|---|---|---|
| Example 3 | • | 59 | — | • | 74 | • | 82 | • |

Example 3

Synthesis of 4'-(6-decyloxy-1,2,3,4-tetrahydro-2-naphthalenecarbonyloxy)-3-fluoro-4-biphenylcarboxylic acid (R)-1-trifluoromethyl-4-ethoxypropyl ester [Exemplified Compound (33)]

Example 4

Synthesis of 4-(6-decyloxy-1,2,3,4-tetrahydro-2-naphthalenecarbonyloxy) cinnamic acid (R)-1-trifluoromethyl-3-methoxypropyl ester [Exemplified Compound (94)]

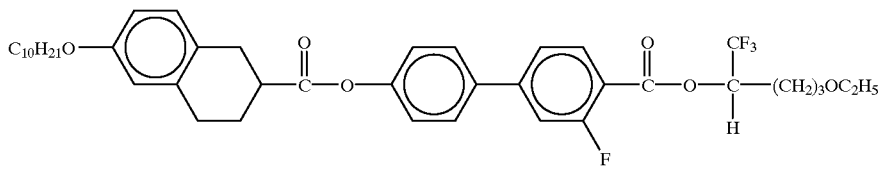

First Stage

To a mixture of 0.66 g (1.2 mmol) of the 4'-(6-decyloxy-1,2,3,4-tetrahydro-2-naphthalenecarbonyloxy)-3-fluoro-4-biphenyl carboxylic acid obtained in the fifth stage of Example 2, 0.22 g (1.2 mmol) of (R)-1-trifluoromethyl-4-ethoxy butanol, and 5 ml of methylene chloride containing 0.02 g (0.016 mmol) of DMAP was dropwise added with

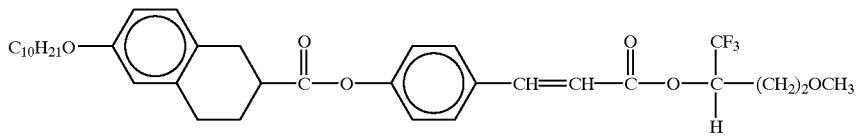

First Stage

To a mixture of 16.5 g (0.101 mol) of 4-hydroxycinnamic acid and 200 ml of a THF solution of 24 ml (0.297 mol) of pyridine was dropwise added 20 ml (0.281 mol) of acetyl chloride over 1 hour at room temperature. After the resulting mixture was stirred at room temperature for 7 hours, the reaction system was poured into 300 ml of a 2N aqueous solution of hydrochloric acid. After extracting with ether and concentrating the organic phase, there was obtained 13.14 g (0.064 mol) of 4-acetoxycinnamic acid as a white solid. The yield was 63%.

Second Stage

To a mixture of 1.06 g (5.15 mmol) of the 4-acetoxycinnamic acid obtained in the first stage, 0.796 g (5.04 mmol) of (R)-trifluorometh1-3-methoxypropanol, 64.3 mg (0.527 mmol) of DMAP and 35 ml of methylene chloride was dropwise added with stirring 15 ml of a methylene chloride solution of 1.11 g (5.39 mmol) of DCC at room temperature. The reaction was further carried out at room temperature for 72 hours. The reaction mixture was filtered and the filtrate thus obtained was concentrated. By purifying the concentrate using column chromatography, 1.16 g (3.35 mmol) of 4-acetoxycinnamic acid (R)-1-trifluoromethyl-3-methoxypropyl was obtained. The yield was 66.5%.

Third Stage 1.16 g (3.35 mmol) of the 4-acetoxycinnamic acid (R)-1-trifluoromethyl-3-methoxypropyl obtained in the second stage was dissolved in 50 ml of diisopropyl ether. To this solution was added 735 mg (10 mmol) of n-butylamine, and the resulting solution was caused to undergo a reaction at room temperature for 12 hours. The reaction mixture was poured into dilute hydrochloric acid, and extraction with ether was carried out. After the organic phase was dried and concentrated, by purifying the concentrate using column chromatography there was obtained 1.06 g (3.49 mmol) of 4-hydroxycinnamic acid (R)-1-trifluoromethyl-3-methoxypropyl ester. The yield was 100%.

Fourth Stage

To a mixture of 0.304 g (1.0 mmol) of the 4-hydroxycinnamic acid (R)-1-trifluoromethyl-3-methoxypropyl ester obtained in the third stage, 0.333 g (1.0 mmol) of the 6-decyloxy-1,2,3,4-tetrahydro-2-naphthalenecarboxylic acid obtained in the first stage of Example 1, 0.017 g (0.14 mmol) of DMAP, and 35 ml of methylene chloride was dropwise added with stirring 10 ml of a methylene chloride solution of 0.250 g (1.2 mmol) of DCC over 2 hours at room temperature. The reaction was further carried out at room temperature for 48 hours. The reaction mixture was filtered, and filtrate thus obtained was concentrated. By purifying the concentrate using column chromatography 0.49 g of a white semisolid was obtained.

This semisolid had an M/e value in FD-mass spectrum of 618.

Figure 4:
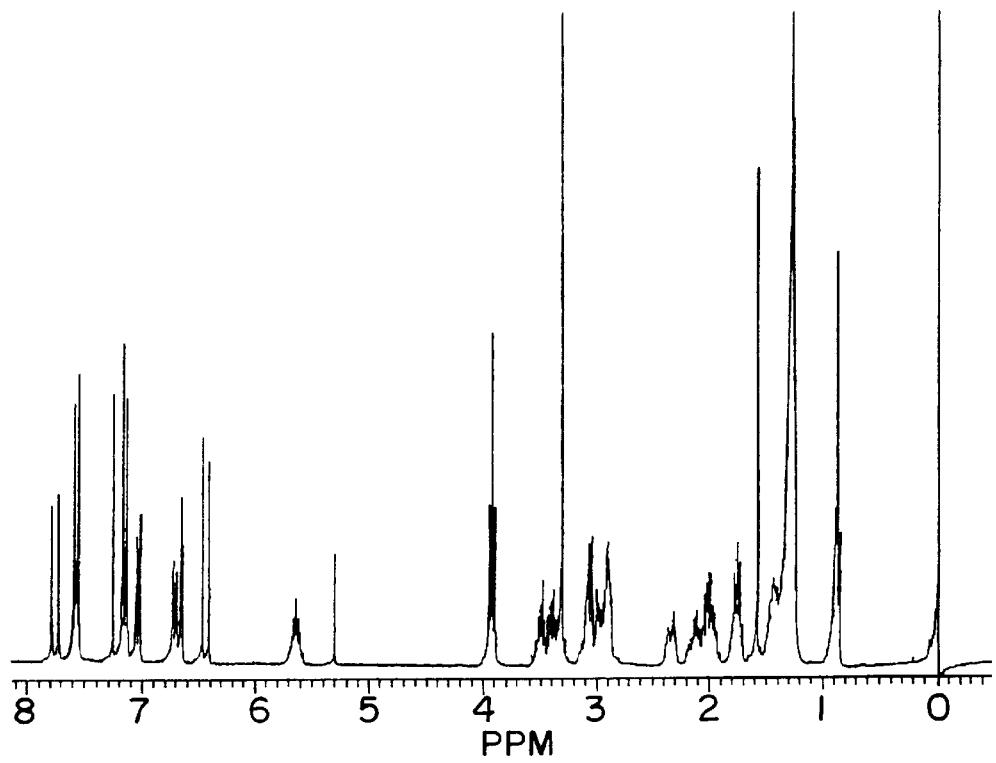
FIG. 4 shows a $^1$H-NMR spectrum of 4-(6-decyloxy-1,2,3,4-tetrahydro-2-naphthalenecarbonyloxy)cinnamic acid (R)-1-trifluoromethyl-3-methoxypropyl ester.

A $^1$H-NMR spectrum of this compound is shown in FIG. 4.

From the analysis of these spectra, this compound was identified as decyloxy-1,2,3,4-tetrahydro-2-naphthalenecarbonyloxy)cinnamic acid (R)-1-trifluoromethyl-3-methoxypropyl ester, the target material [Exemplified Compound (94)]. The yield was 79%.

The phase transition temperatures of this liquid crystal compound are set forth in Table 14.

TABLE 14

|  | Cry | SmC$_A$* | SmC* | SmA | Iso |
|---|---|---|---|---|---|
| Example 4 | • | 34 | — | — | • (25) • |

Example 5

Synthesis of 4-(6-decyloxy-1,2,3,4-tetrahydro-2-naphthalenemethyleneoxy) cinnamic acid (R)-1-trifluoromethyl-3-methoxypropyl ester [Exemplified Compound (109)]

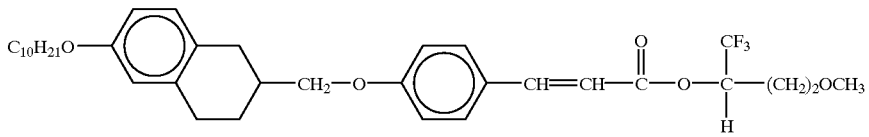

First Stage 0.34 g (8.95 mmol) of lithium aluminum hydride was added to 40 ml of ether. To this mixture was slowly added 2.54 g (7.65 mmol) of the 6-decyloxy-1,2,3,4-tetrahydro-2-naphthalenecarboxylic acid obtained in the first stage of Example 1. After the resulting mixture was stirred at room temperature for 30 minutes, it was heated under reflux for 6 hours. After cooling, the reaction mixture was caused to undergo hydrolysis and extraction with ether. The organic phase was concentrated and by purifying the concentrate using column chromatography there was obtained 2.31 g (7.26 mmol) of 6-decyloxy-1,2,3,4-tetrahydro-2-hydroxymethylnaphthalene as a white solid.

Second Stage

A mixture of 0.26 g (0.83 mmol) of the 6-decyloxy-1,2,3,4-tetrahydro-2-hydroxymethylnaphthalene obtained in the first stage, 0.26 g (0.85 mmol) of the 4-hydroxycinnamic acid (R)-1-trifluoromethyl-3-methoxypropyl ester obtained in the third stage of Example 4 and 0.29 g (1.11 mmol) of triphenylphosphine was dissolved in THF. To the resulting mixture was added dropwise from a syringe with stirring at room temperature 150 μL (0.96 mmol) of diethylazocarboxylic acid. After the mixture was stirred overnight at room temperature, it was concentrated and by purifying the concentrate using column chromatography there was obtained 0.27 g of a white semisolid. This semisolid had an M/e value in FD-mass spectrum of 604.

Figure 5:
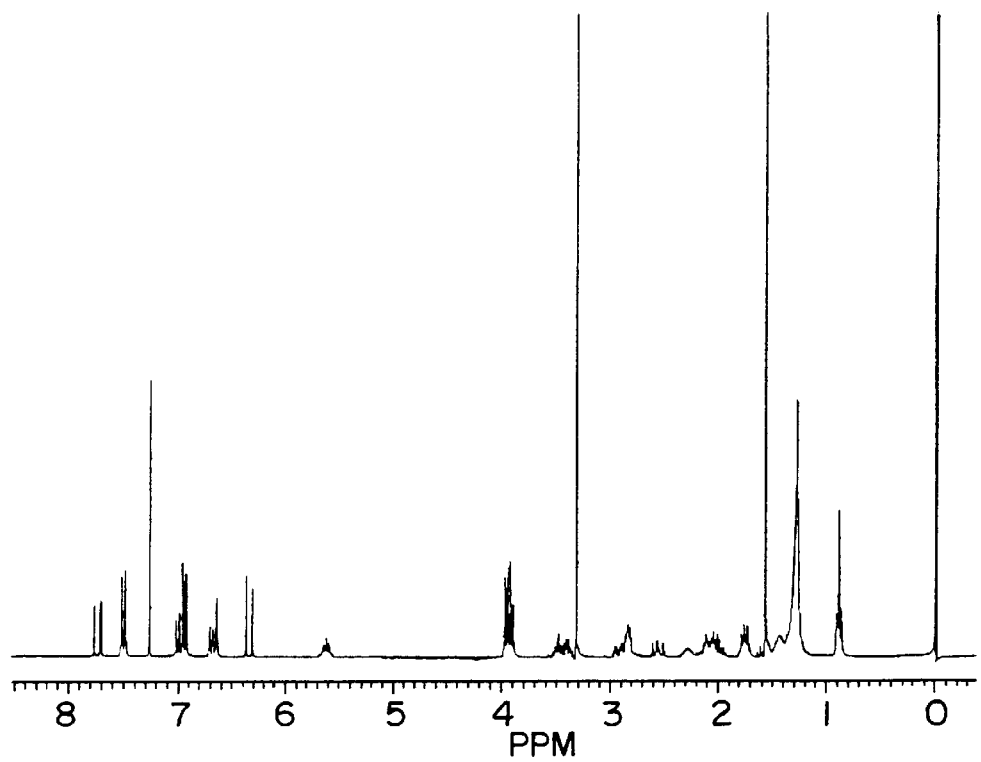
FIG. 5 shows a $^1$H-NMR spectrum of 4-(6-decyloxy-1,2,3,4-tetrahydro-2-naphthalenemethyleneoxy)cinnamic acid (R)-1-trifluoromethyl-3-methoxypropyl ester.

A $^1$H-NMR spectrum of this compound is shown in FIG. 5.

From the analysis of these spectra, this compound was identified as 4-(6-decyloxy-1,2,3,4-tetrahydro-2-naphthalenemethyleneoxy)cinnamic acid (R)-1-trifluoromethyl-3-methoxypropyl ester, the target material [Exemplified Compound (109)]. The yield was 53%.

The phase transition temperatures of this liquid crystal compound are set forth in Table 15.

TABLE 15

|  | Cry | SmC$_A$* | SmC* | SmA | Iso |
|---|---|---|---|---|---|
| Example 5 | • | 50 | — | — | • | 60 | • |

Example 6

Synthesis of 4'-(6-decyloxy-1,2,3,4-tetrahydro-2-naphthalenemethyleneoxy)-4-biphenylcarboxylic acid (R)-1-trifluoromethyl-3-methoxypropyl ester [Exemplified Compound (19)]

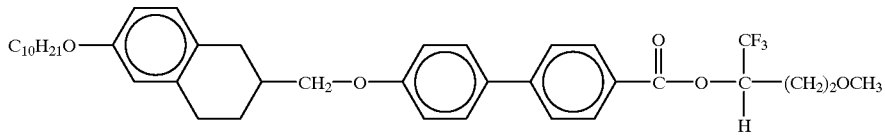

First Stage

A mixture of 10.7 g (50 mmol) of 4'-hydroxy-4-biphenylcarboxylic acid, 34.2 g (200 mmol) of benzynyl bromide and 27.6 g (200 mmol) of potassium carbonate was added to 150 ml of N,N'-dimethylformamide. This solution was refluxed with stirring for 13 hours. After cooling, 200 ml of water was added and a precipitated solid was filtered out. A mixture of the solid thus obtained, 8 g (121 mmol) of potassium hydroxide (purity: 85%) and 80 ml of water was added to 400 ml of ethanol. This solution was stirred under reflux for 3 hours. After cooling, the precipitated solid was filtered out. To the filtrate 400 ml of THF was added along with 100 ml of ethanol and 10 ml of hydrochloric acid. The mixture was stirred under reflux for 1 hour. After the reaction mixture was allowed to stand for cooling to room temperature, 4'-benzyloxy-4-biphenylcarboxylic acid precipitated as a colorless crystalline matter. The quantity produced was 10.3 g and the yield was 68%.

Second Stage

To a mixture of 2.22 g (7.3 mmol) of the 4'-benzyloxy-4-biphenylcarboxylic acid obtained in the first stage, 1.22 g (7.7 mmol) of (R)-trifluorometh1-3-methoxypropanol, 0.46 g (3.77 mmol) of DMAP and 40 ml of methylene chloride, there was dropwise added with stirring at room temperature 20 ml of a methylene chloride solution of 0.173 g (8.40 mmol) of DCC. The reaction was further carried out at room temperature for 24 hours. The reaction mixture was filtered and the filtrate thus obtained was concentrated. By purifying the concentrate using column chromatography, 2.93 g (6.60 mmol) of 4'-benzyloxy-4-biphenylcarboxylic acid (R)-1-trifluoromethyl-3-methoxypropyl ester was obtained. The yield was 90%.

Third Stage

A mixture of 2.93 g (6.60 mmol) of the 4'-benzyloxy-4-biphenylcarboxylic acid (R)-1-trifluoromethyl-3-methoxypropyl ester obtained in the second stage and 0.4 g of 5% palladium/carbon as catalyst was added to 50 ml of THF. The solution was placed in a hydrogen atmosphere, using a hydrogen baloon, and was stirred at room temperature overnight. After filtering out the catalyst and concentrating the filtrate, there was obtained approximately quantitatively 4'-hydroxy-4-biphenylcarboxylic acid (R)-1-trifluoromethyl-3-methoxypropyl ester.

Fourth Stage

A mixture of 0.29 g (0.81 mmol) of the 4'-hydroxy-4-biphenylcarboxylic acid (R)-1-trifluoromethyl-3-methoxypropyl ester obtained in the third stage, 0.26 g (0.82 mmol) of the 6-decyloxy-1,2,3,4-tetrahydro-2-hydroxymethylnaphthalene obtained in the first stage of Example 5, and 0.29 mg (1.10 mmol) of triphenylphosphine was added to 10 ml of THF. While stirring the resulting mixture at room temperature, 170 μL (1.10 mmol) of diethylazodicarboxylic acid was added from a syringe. After further stirring the mixture at room temperature overnight, the solvent was removed by fractionation. Then, by means of purification using column chromatography, 0.20 g of a colorless semisolid was obtained.

This semisolid had an M/e value in FD-mass spectrum of 654.

Figure 6:
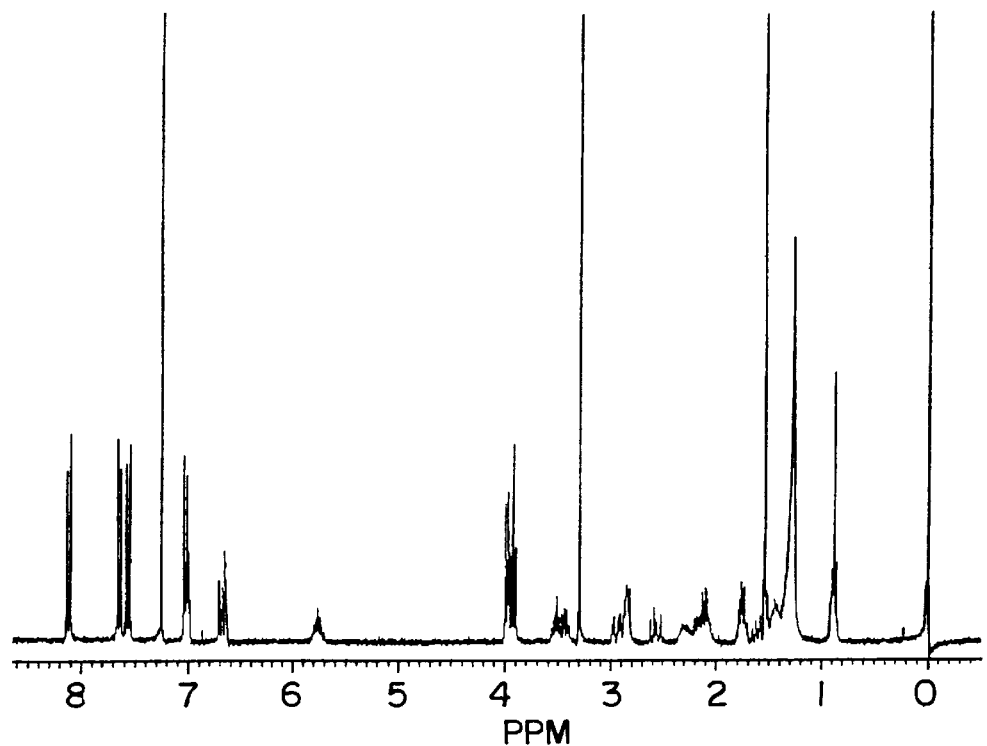
FIG. 6 shows a $^1$H-NMR spectrum of 4'-(6-decyloxy-1,2,3,4-tetrahydro-2-naphthalenemethyleneoxy)-4-biphenylcarboxylic acid (R)-1-trifluoromethyl-3-methoxypropyl ester.

A $^1$H-NMR spectrum of this compound is shown in FIG. 6.

From the analysis of these spectra, this compound was identified as 4'-(6-decyloxy-1,2,3,4-tetrahydro-2-naphthalenemethyleneoxy)-4-biphenylcarboxylic acid (R)-1-trifluoromethyl-3-methoxypropyl ester, the target material [Exemplified Compound (19)]. The yield was 38%.

The phase transition temperatures of this liquid crystal compound are set forth in Table 16.

TABLE 16

|  | Cry | SmC$_A$* | SmC* | SmA | Iso |
|---|---|---|---|---|---|
| Example 6 | • | 104 | — | — | — | • |

Example 7

Synthesis of 4'-(6-decanoyl-1,2,3,4-tetrahydro-2-naphthalenecarbonyloxy)-4-biphenylcarboxylic acid (R)-1-trifluoromethyl-4-ethoxybutyl ester

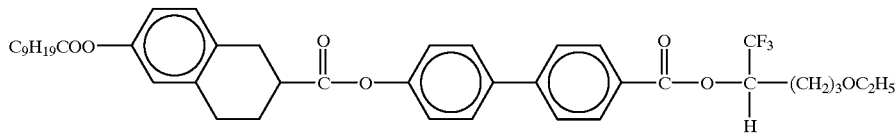

First Stage

A mixed solution of 16.6 g (50 mmol) of the 6-decyloxy-1,2,3,4-tetrahydro-2-naphthalenecarboxylic acid obtained in the first stage of Example 1, 86.5 g (500 mmol) of 47% hydrobromic acid and 250 m of acetic acid was heated under reflux for 10 hours. After cooling, the reaction mixture was washed twice with hexane, and the water phase was concentrated. The obtained solid was dried to obtain 7.88 g (41 mmol) of 6-hydroxy-1,2,3,4-tetrahydro-2-naphthalenecarboxylic acid. The yield was 82%.

Second Stage

A mixture of 6.12 g (31.9 mmol) of the 6-hydroxy-1,2,3,4-tetrahydro-2-naphthalenecarboxylic acid obtained in the first stage, 35.7 g (331 mmol) of benzyl alcohol, and 0.21 g (0.43 mmol) of dibutyltin oxide was heated with stirring at a temperature of 195° C. for 6 hours. After removing benzyl alcohol by fractionation under a reduced pressure, the residue was purified using column chromatography, and there was obtained 8.1 g (28.7 mmol) of 6-hydroxy-1,2,3,4-tetrahydro-2-naphthalenecarboxylic acid benzyl ester. The yield was 90%.

Third Stage 2.51 g (13.2 mmol) of decanoyl chloride and 5 ml (62 mmol) of pyridine were added to 20 ml of toluene. To this mixture, 10 ml of a toluene solution of 2.67 g (9.47 mmol) of the 6-hydroxy-1,2,3,4-tetrahydro-2-naphthalenecarboxylic acid benzyl ester obtained in the second stage was added at room temperature. The mixture was caused to undergo hydrolysis with stirring at room temperature for 24 hours. After drying, concentrating and purifying using column chromatography the organic phase, there was obtained 3.79 g (8.69 mmol) of 6-decanoyl-1,2,3,4-tetrahydro-2-naphthalenecarboxylic acid benzyl ester. The yield was 92%.

Fourth Stage 50 mL of a THF solution containing 3.79 g (8.69 mmol) of 6-decanoyl-1,2,3,4-tetrahydro-2-naphthalenecarboxylic acid benzyl ester and 0.43 g of 5% palladium/carbon was placed in a hydrogen atmosphere, using a baloon, and was stirred at room temperature for 24 hours. The reaction mixture was filtered and by concentrating the filtrate, there was obtained 3.19 g of 6-decanoyl-1,2,3,4-tetrahydro-2-naphthalenecarboxylic acid. The yield was 100%.

Fifth Stage

To a mixture of 0.28 g (0.81 mmol) of the 6-decanoyl-1,2,3,4-tetrahydro-2-naphthalenecarboxylic acid obtained in the fourth stage, 0.30 g (0.79 mmol) of the 4'-hydroxy-4-biphenylcarboxylic acid (R)-1-trifluoromethy-4-ethoxybutyl ester which was obtained by carrying out the same reaction as in the second stage and the third stage of Example 6 excepting that (R)-1-tiifluorometyyl-4-ethoxy butanol was used in place of (R)-trifluoromethyl-3-methoxypropanol, 0.099 g (0.81 mmol) of DMAP, and 10 ml of methylene chloride, there was slowly dropwise added with stirring at room temperature 5 ml of a methylene chloride solution of 0.23 g (1.11 mmol) of DCC. The reaction was further carried out for 48 hours. The reaction mixture was filtered and the filtrate thus obtained was concentrated. By purifying the concentrate using column chromatography, 0.40 g of a white semisolid was obtained.

This semisolid had an M/e value in FD-mass spectrum of 710.

Figure 7:
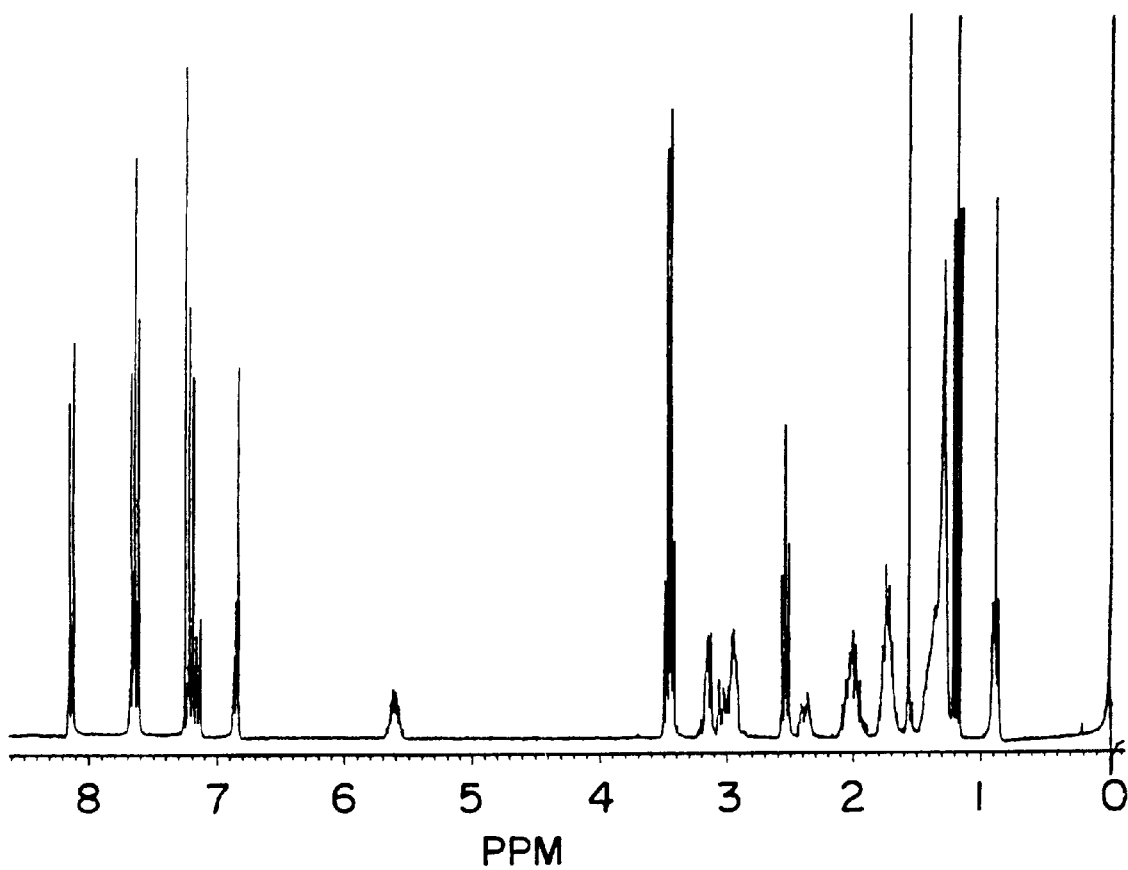
FIG. 7 shows a $^1$H-NMR spectrum of 4'-(6-decanoyl-1,2,3,4-tetrahydro-2-naphthalenecarbonyloxy)-4-biphenylcarboxylic acid (R)-1-trifluoromethyl-4-ethoxybutyl ester.

A $^1$H-NMR spectrum of this compound is shown in FIG. 7.

From the analysis of these spectra, this compound was identified as 4'-(6-decanoyl-1,2,3,4-tetrahydro-2-naphthalenecarbonyloxy)-4-biphenylcarboxylic acid (R)-1-trifluoromethyl-4-ethoxybutyl ester, the target material. The yield was 72%.

The phase transition temperature of this liquid crystal compound are set forth in Table 17.

TABLE 17

|  | Cry |  | SmC$_A$* | SmC* |  | SmA |  | Iso |
|---|---|---|---|---|---|---|---|---|
| Example 7 | • | 69 | — | • | (59) | • | 104 | • |

Example 8

A liquid crystal composition was prepared by mixing an antiferroelectric liquid crystal represented by the following formula [A-1] with the compound represented by the following formula [B-1] which is the compound synthesized in Example 1 by a mixing ratio of 40 mol%. Results are shown in Table 18.

[A-1]

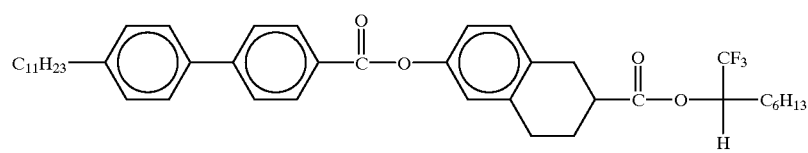

-continued

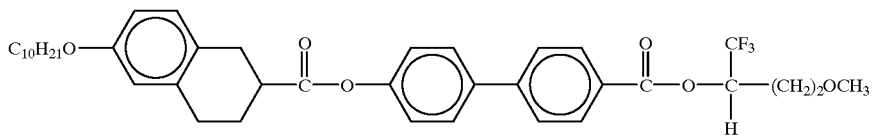
[B-1]

Comparative Example 1

A liquid crystal composition was prepared in accordance with the same procedure as Example 8, except that a compound represented by the following formula [C-1] was used in place of the compound represented by the formula [B-1] in Example 8. Results are shown in Table 18.

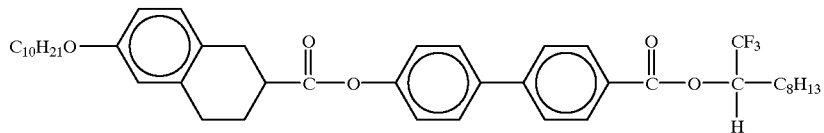
[C-1]

TABLE 18

| | Phase Transition Temperatures | | | | | | | Threshold |
|---|---|---|---|---|---|---|---|---|
| | Cry | SmC$_A$* | | SmC* | SmA | | Iso | Voltage (30° C.) |
| Example 8 | — | • 69 | | — | • 102 | | • | 11.9 V/2 μm |
| Comparative Example 1 | — | • 70 | | — | • 99 | | • | 19.1 V/2 μm |

Example 9

A composition [A] was prepared by mixing the compound [A-2] with the compound [A-3] represented by the following formula by the composition ratios set forth below. The phase transition temperatures of this composition [A] were Cry (35° C.), SmCA* (106° C.), SmA (114° C.) and Iso.

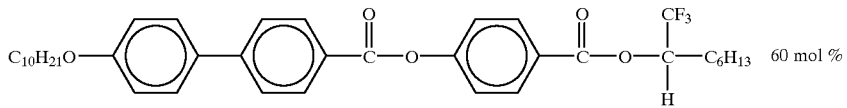
[A-2] 60 mol %

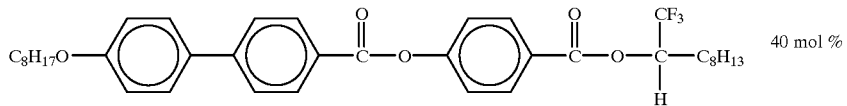
[A-3] 40 mol %

A liquid crystal composition was prepared by mixing the obtained composition [A] with the following compound [B-2] synthesized in Example 4 by a mole ratio of 20 mol%.

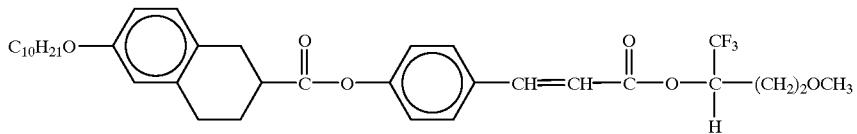

[B-2]

Comparative Example 2

A liquid crystal composition was prepared in accordance with the same procedure as Example 9, except that a compound represented by the following formula [C-2] was used in place of the compound represented by the formula [B-2] in Example 9. Results are shown in Table 19.

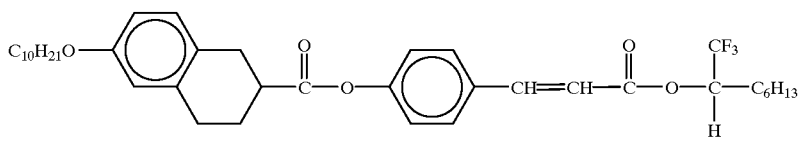

[C-2]

TABLE 19

| | Phase Transition Temperatures | | | | | Response time | Threshold |
|---|---|---|---|---|---|---|---|
| | Cry | SmC$_A$* | SmC* | SmA | Iso | (30° C., 40 V) | Voltage (30° C.) |
| Example 9 | • | • 90 | — | • 99 | • | 146 μsec | 29.3 V/2 μm |
| Comparative Example 2 | • | • 84 | — | • 94 | • | 454 μsec | 32.6 V/2 μm |

Example 10

A composition [B] was prepared by mixing the compounds [A-4] and [A-5] represented by the following formulas, respectively, by a mole ratio of 70/30 between them.

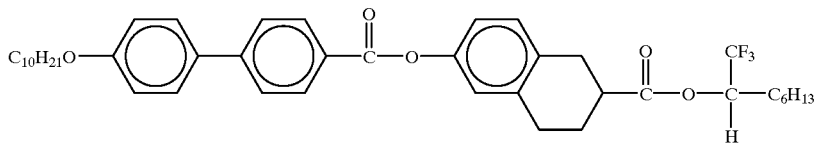

[A-4]

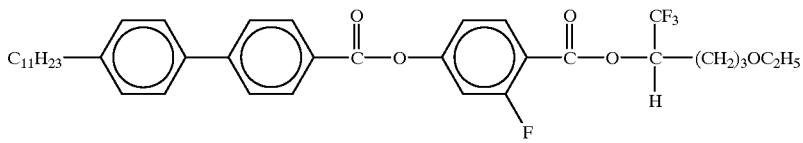

[A-5]

A liquid crystal composition was prepared by mixing a compound [B-3] represented by the following formula with the composition [B] thus obtained by a mole ratio of 20%. Results are shown in Table 20.

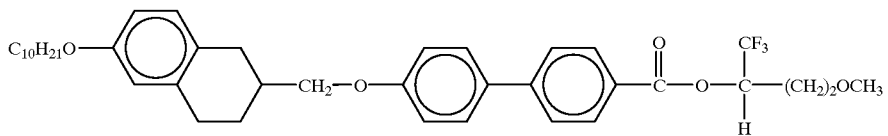
[B-3]

TABLE 20

| | Phase Transition Temperatures | | | | | | | Threshold |
|---|---|---|---|---|---|---|---|---|
| | Cry | SmC$_A$* | | SmCγ* | | SmA | Iso | Voltage (30° C.) |
| Example 10 | • | • | 81 | • 88 | • | 110 | • | 14.8 V/2 μm |

Example 11

A composition [C] was prepared by mixing compounds [A-6] and [A-7] represented by the following formulas, respectively, by a mole ratio of 70/30 between them.

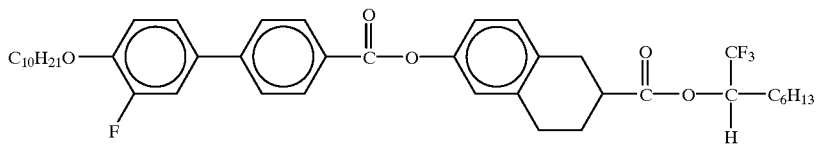
[A-6]

[A-7]

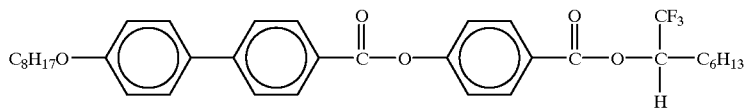

A liquid crystal composition was prepared by mixing a compound [B-4] represented by the following formula with the composition [C] thus obtained by a mole ratio of 20%. Results are shown in Table 21.

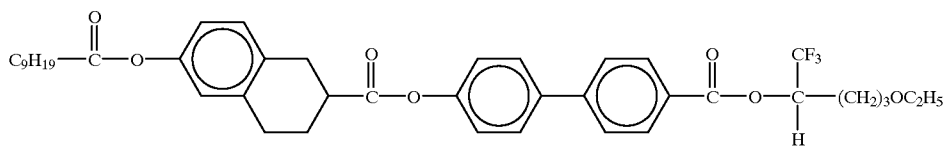
[B-4]

TABLE 21

| | Phase Transition Temperatures | | | | | | | Threshold |
|---|---|---|---|---|---|---|---|---|
| | Cry | SmC$_A$* | | SmC* | | SmA | Iso | Voltage (30° C.) |
| Example 11 | • | • | 74 | • | 84 | • 116 | • | 12.5 V/2 μm |

Example 12

A composition [D] was prepared by mixing compounds [A-8] and [A-9] represented by the following formulas, respectively, by a mole ratio of 70/30 between them.

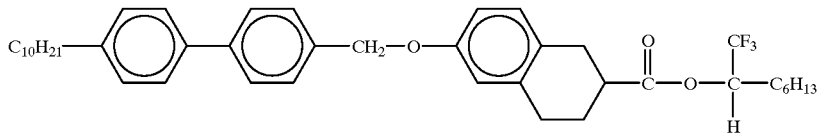

[A-8]

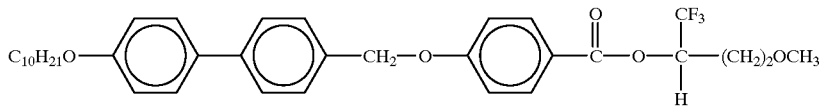

[A-9]

A liquid crystal composition was prepared by mixing a compound [B-5] represented by the following formula with the composition [D] thus obtained by a mole ratio of 20%. Results are shown in Table 22.

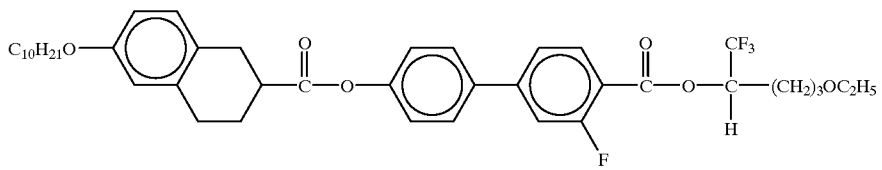

[B-5]

TABLE 22

| | Phase Transition Temperatures | | | | | | | | Threshold |
|---|---|---|---|---|---|---|---|---|---|
| | Cry | SmC$_A$* | | SmC* | | SmA | | Iso | Voltage (30° C.) |
| Example 12 | — | • | 55 | • | 68 | • | 79 | • | 9.9 V/2 μm |

Example 13

A composition [E] was prepared by mixing compounds [A-8] and [A-10] represented by the following formulas, respectively, by a mole ratio of 80/20 between them.

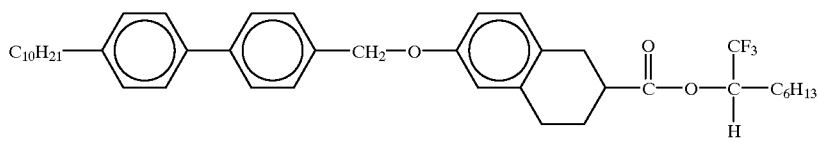

[A-8]

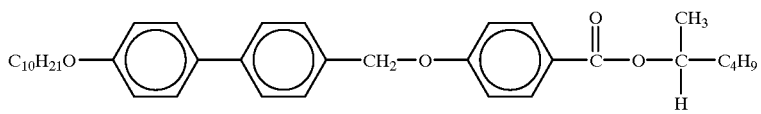

[A-10]

A liquid crystal composition was prepared by mixing a compound [B-1] represented by the following formula with the composition [E] thus obtained by a mole ratio of 30%. Results are shown in Table 23.

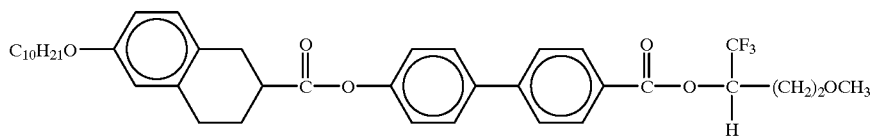
[B-1]

TABLE 23

| | Phase Transition Temperatures | | | | | | | | Threshold |
|---|---|---|---|---|---|---|---|---|---|
| | Cry | SmC$_A$* | | SmC* | | SmA | | Iso | Voltage (30° C.) |
| Example 13 | — | • | 61 | • | 68 | • | 88 | • | 11.3 V/2 μm |

Example 14

A composition [F] was prepared by mixing compounds [A-11], [A-12], and [A-13] represented by the following formulas, respectively, by a mole ratio of 60/15/25 among them.

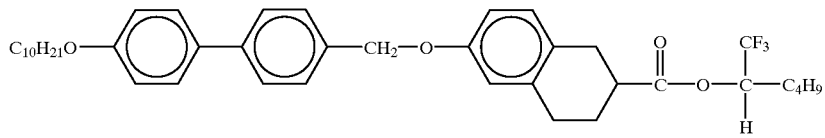
[A-11]

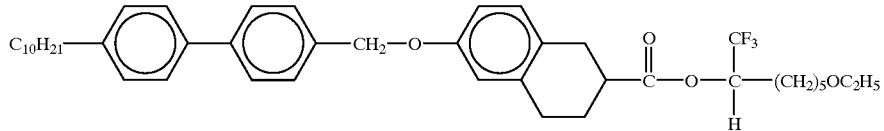
[A-12]

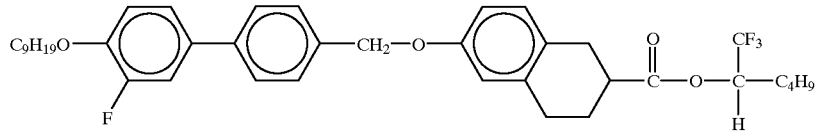
[A-13]

A liquid crystal composition was prepared by mixing a compound [B-4] represented by the following formula with the composition [F] thus obtained by a mole ratio of 20%. Results are shown in Table 24.

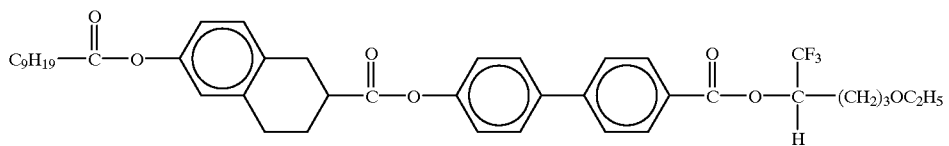

[B-4]

TABLE 24

| | Phase Transition Temperatures | | | | | | | | Threshold |
|---|---|---|---|---|---|---|---|---|---|
| | Cry | | SmC$_A$* | | SmC* | | SmA | Iso | Voltage (30° C.) |
| Example 14 | • | • | 56 | • | 74 | • | 95 | • | 8.8 V/2 μm |

Example 15

A composition [G] was prepared by mixing compounds [A-14], [A-15], and ferroelectric liquid crystal ZLI-3489 (product of Merck), respectively, by a weight ratio of 85/10/5 among them.

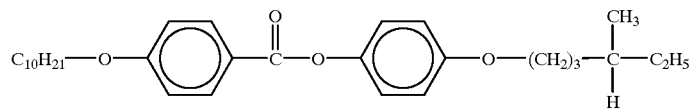

[A-14]

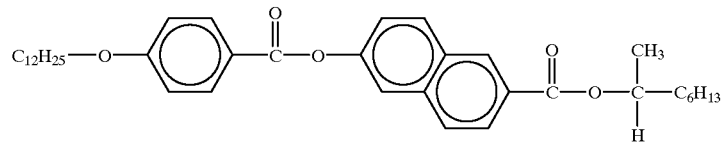

[A-15]

A liquid crystal composition was prepared by mixing a compound [B-5] represented by the following formula with the composition [G] thus obtained by 10% by weight. Results are shown in Table 25.

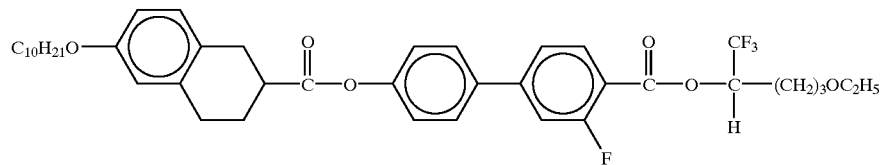

[B-5]

Comparative Example 3

A composition [G] prepared in Example 25 is used. Results are shown in Table 25.

TABLE 25

| | Phase Transition Temperatures | | | Response time | Memory Stability |
|---|---|---|---|---|---|
| | Cry Iso | SmC$_A$* | SmC* | SmA | (30° C., 40 V) | (30° C.) |
| Example 25 | — | — | • 47 • | 78 • | 186 μsec | 99 |
| Comparative Example 3 | — | — | • 64 • | 73 • | 4.8 msec | 52 |

Memory stability is defined as relative ratio of light transmission at one sec. after turning off voltage to at 5 msec. driving voltage of 10 V.

What we claim is:

1. A tetralin compound represented by the following formula [I]:

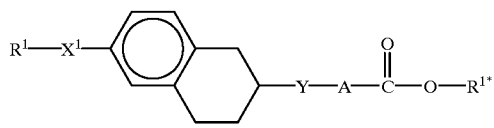

wherein

R$^1$ is an alkyl group or a polyfluoroalkyl group of 3–20 carbon atoms (wherein a single or 2 or more mutually nonadjacent —CH$_2$— or —CF$_2$— existing in that group may be substituted with —O—), X$^1$ is —COO—, —O— or a single bond, A is each independently a group selected from the group consisting of

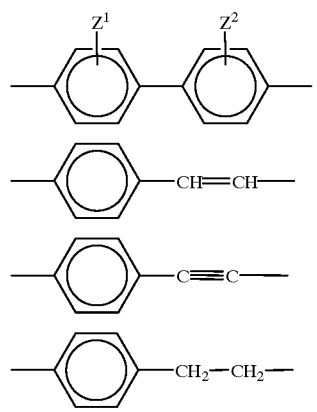

(wherein Z$^1$ and Z$^2$ are each independently a hydrogen atom or a fluorine atom), Y is a group selected from the group consisting of —COO—, —CH$_2$O—, —OCH$_2$, and —CH$_2$CH$_2$—, and R$^{1*}$ is an optically active group represented by the following formula [II]

—C*H—(CF$_3$)—(CH$_2$)$_m$—O—C$_n$H$_{2n+1}$ [II]

(wherein m is an integer of 2–5, and n is an integer of 1–3).

2. The tetralin compound as defined in claim 1, wherein R$^{1*}$ in the formula [II] in claim 1 is a group selected from the following group:

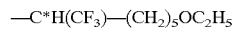

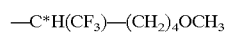

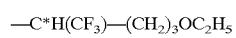

—C*H(CF$_3$)—(CH$_2$)$_2$OCH$_3$, and

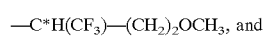

3. A liquid crystal material which is represented by the formula [I] in claim 1:

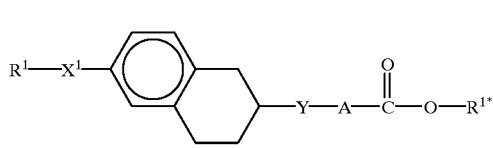

wherein R$^1$ is an alkyl group or a polyfluoroalkyl group of 3 to 20 carbon atoms (wherein a single or 2 or more mutually nonadjacent —CH$_2$— or —CF$_2$ may be substituted with —O—, X$^1$ is —COO—, —O—, or a single bond, A is each independently a group selected from the group consisting of

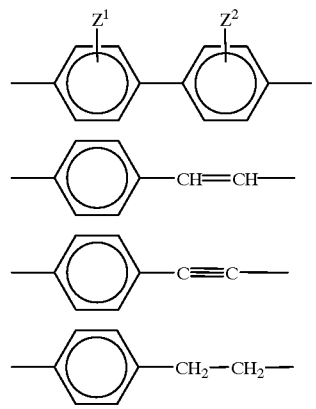

Z$^1$ and Z$^2$ are each independently a hydrogen atom or a fluorine atom, Y is a group selected from the group consisting of —COO—, —CH$_2$O—, —OCH$_2$—, and —CH$_2$CH$_2$—, and R$^{1*}$ is an optically active group represented by the following formula [II]

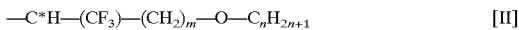  [II]

(wherein m is an integer of 2–5, and n is an integer of 1–3).

4. The liquid crystal material as defined in claim 3, wherein R$^{1*}$ in the formula [II] is a group selected from the group consisting of

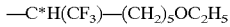

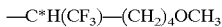

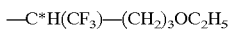

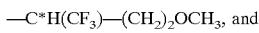

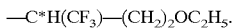

5. A liquid crystal composition comprising the compound represented by the formula [I] defined in claim 1 or claim 2 and (an)other liquid crystal compound(s) and/or additive(s).

6. A ferroelectric liquid crystal composition comprising the compound represented by the formula [I] defined in claim 1 or claim 2 and (an)other liquid crystal compound(s) and/or additive(s).

7. A antiferroelectric liquid crystal composition comprising the compound represented by the formula [I] defined in claim 1 or claim 2 and (an)other liquid crystal compound(s) and/or additive(s).

8. An antiferroelectric liquid crystal composition comprising the compound represented by the formula [I] defined claim 1 or claim 2 and a compound represented by the following formula [III]

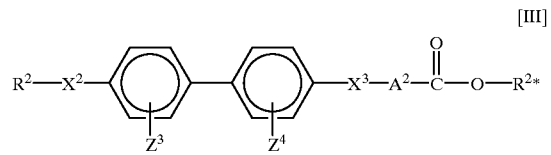

wherein R$^2$ is an alkyl group or a polyfluoroalkyl group of 3–20 carbon atoms (wherein a single or mutually nonadjacent —CH$_2$— may be substituted with —O—), A$^2$ is a group selected from the group consisting of the following:

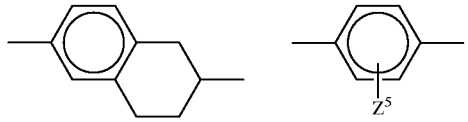

(wherein Z$^3$, Z$^4$, and Z$^5$ are each independently a hydrogen atom or a fluorine atom), X$^2$ is —COO—, —O—, or a single bond, X$^3$ is —COO— or —CH$_2$O—, R$^{2*}$ is an optically active group represented by the following formula [IV] (wherein when V is CF$_3$, p=1 and r≠0, or p=0 and r=0, and when V is CH$_3$, p=0 and r=0)

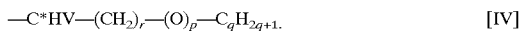  [IV]

* * * * *